United States Patent [19]
Zhang et al.

[11] Patent Number: 5,623,054
[45] Date of Patent: Apr. 22, 1997

[54] CRUCIFER AFT PROTEINS AND USES THEREOF

[75] Inventors: Hong Zhang, Boston; Howard M. Goodman, Newton Center, both of Mass.

[73] Assignee: The General Hospital Corporation, Boston, Mass.

[21] Appl. No.: 266,451

[22] Filed: Jun. 23, 1994

[51] Int. Cl.⁶ .......................... C07K 14/415; C12N 15/00
[52] U.S. Cl. .......................... 530/370; 530/377; 435/69.1; 435/172.3
[58] Field of Search .................. 435/172.3, 69.1; 530/370, 377

[56] References Cited

U.S. PATENT DOCUMENTS 4,990,607  2/1991  Katagiri et al. ..................... 536/27

FOREIGN PATENT DOCUMENTS

0475584A3  3/1992  European Pat. Off. .
0589841A3  3/1994  European Pat. Off. .

OTHER PUBLICATIONS

Altken et al., (1992) TIBS 17:498–501.
Brandt et al., (1992) The Plant Journal 2:815–820.
de Vetten et al., (1992) The Plant Cell, 4:1295–1307.
Hirsch et al., (1992) FEBS Letters 296:222–224.
Ichimura et al., (1988) Proc. Natl. Acad. Sci. USA, 85:7084–7088.
Lu et al., (1992) Proc. Natl. Acad. Sci. USA, 89:11490–11494.
McCarty et al., (1991) Cell 66:895–905.
Ma et al., (1988) Nature 334:631–633.
Toker et al., (1992) Eur. J. Biochem., 206:453–461.
Zupan et al., (1992) The Journal of Biological Chemistry, 267:8707–8710.
Lu et al., The Plant Cell 6:501–510 (1994).
Goff et al., Genes & Development 6:864–875 (1992).
Goff et al., Genes & Development 5:298–309 (1991).
Zhang et al., Biochimica et Biophysica Acta 1266:113–116 (1995).
Jarillo et al., Plant Molecular Biology 25:693–704 (1994).

*Primary Examiner*—David T. Fox
*Assistant Examiner*—Elizabeth F. McElwain
*Attorney, Agent, or Firm*—Fish & Richardson P.C.

[57] ABSTRACT

Purified DNA encoding crucifer AFT proteins and chimeric transcriptional activator proteins from such DNA are disclosed. Such proteins are also involved in plant defense mechanisms by interacting with proteins involved in protecting plants from pathogens. The recombinant polypeptides and fragments are useful in methods of modulating plant gene expression.

6 Claims, 11 Drawing Sheets

(SEQ ID NO: 1)
```
  1 AAAAAAAAAATCAAATCTCTCTCTTTCTCTCTCTAATGGCGGCGACATTAGGCAGAGACCA
                                       M  A  A  T  L  G  R  D  Q   9
                                                      (SEQ ID NO: 2)
 61 GTATGTGTACATGGCGAAGCTCGCCGAGCAGGCGGAGCGTTACGAAGAGATGGTTCAATT
     Y  V  V  M  A  K  L  A  E  Q  A  E  R  Y  E  E  M  V  Q  F   29
121 CATGGAACAGCTCGTTACAGGCGCTACTCCAGCGGAAGAGCTCACCGTTGAAGAGAGGAA
     M  E  Q  L  V  T  G  A  T  P  A  E  E  L  T  V  E  E  R  N   49
181 TCTCCTCTCTGTTGCTTACAAGAACGTGATCGGATCTCTACGCGCCGCCTGGAGGATCGT
     L  L  S  V  A  Y  K  N  V  I  G  S  L  R  A  A  W  R  I  V   69
241 GTCTTCGATTGAGCAGAAGGAAGAGAGTAGGAAGAACGACGAGCACGTGTCGCTTGTCAA
     S  S  I  E  Q  K  E  E  S  R  K  N  D  E  H  V  S  L  V  K   89
301 GGATTACAGATCTAAAGTTGAGTCTGAGCTTTCTTCTGTTTGCTCTGGAATCCTTAAGCT
     D  Y  R  S  K  V  E  S  E  L  S  S  V  C  S  G  I  L  K  L   109
361 CCTTGACTCGCATCTGATCCCATCTGCTGGAGCGAGTGAGTCTAAGGTCTTTTACTTGAA
     L  D  S  H  L  I  P  S  A  G  A  S  E  S  K  V  F  Y  L  K   129
421 GATGAAAGGTGATTATCATCGGTACATGGCTGAGTTTAAGTCTGGTGATGAGAGGAAAAC
     M  K  G  D  Y  H  R  Y  M  A  E  F  K  S  G  D  E  R  K  T   149
481 TGCTGCTGAAGATACCATGCTCGCTTACAAAGCAGCTCAGGATATCGCAGCTGCGGATAT
     A  A  E  D  T  M  L  A  Y  K  A  A  Q  D  I  A  A  A  D  M   169
541 GGCACCTACTCATCCGATAAGGCTTGGTCTGGCCCTGAATTTCTCAGTGTTCTACTATGA
     A  P  T  H  P  I  R  L  G  L  A  L  N  F  S  V  F  Y  Y  E   189
601 GATTCTCAATTCTTCAGACAAAGCTTGTAACATGGCCAAACAGGCTTTTGAGGAGGCCAT
     I  L  N  S  S  D  K  A  C  N  M  A  K  Q  A  F  E  E  A  I   209
661 AGCTGAGCTTGACACTCTGGGAGAGGAATCCTACAAAGACAGCACTCTCATAATGCAGTT
     A  E  L  D  T  L  G  E  E  S  Y  K  D  S  T  L  I  M  Q  L   229
721 GCTGAGGGACAATTTAACCCTTTGGACCTCCGATATGCAGGAGCAGATGGACGAGGCCTG
     L  R  D  N  L  T  L  W  T  S  D  M  Q  E  Q  M  D  E  A     248
781 AGGATCTAGATGAAGGGGGGAGGGTTGTTACGCGATGTTTCTGCCACCAAATCGATCTC
841 AAAAT
```

FIG. 1

| B42/AFT1 Derivatives | | Growth | β-Galactosidase |
|---|---|---|---|
| B42/1-248 | 1 — 248 | + | 10.9 |
| B42/1-121 | 1 — 121 | − | 1.7 |
| B42/34-248 | 34 — 248 | + | 21.2 |
| B42/122-248 | 122 — 248 | + | 15.3 |
| B42/34-194 | 34 — 194 | − | 1.8 |
| B42 alone | | − | 1.7 |

FIG. 3A

| LexA/AFT1 Derivatives | | Growth | β-Galactosidase |
|---|---|---|---|
| LexA/1-248 | 1 — 248 | + | 39.2 |
| LexA/1-194 | 1 — 194 | − | 0.7 |
| LexA/1-121 | 1 — 121 | − | 0.6 |
| LexA/34-248 | 34 — 248 | + | 9.3 |
| LexA/122-248 | 122 — 248 | − | 1.2 |
| LexA alone | | − | 0.8 |

FIG. 3B

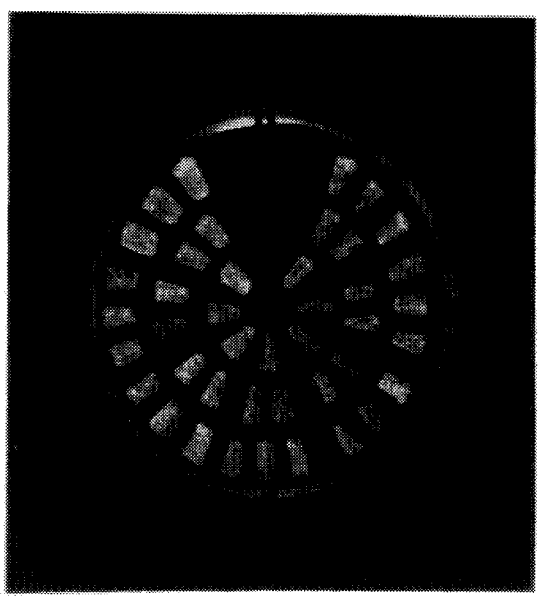
FIG. 2
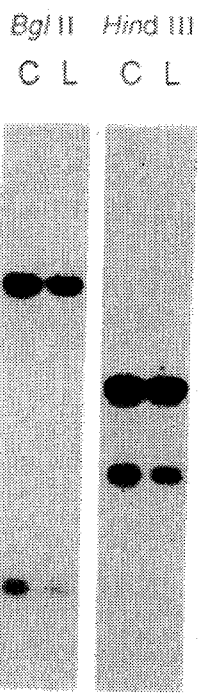
FIG. 4
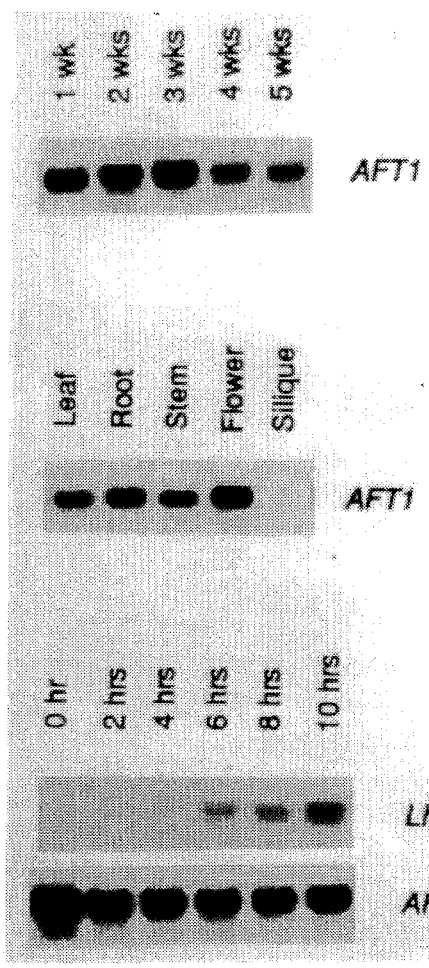
FIG. 5A
FIG. 5B
FIG. 5C

```
  1  TCACCCAGAG AGGTCAGGCT TTGATGGACC ATGGACCCAA GAGCCGCTGA
 51  AGTTTGACAA CTCCTACTTC GTGGAACTGC TGAAAGGAGA ATCAGAGGGC
101  TTGTTGAAAC TTCCAACTGA CAAGACCTTA TTGGAAGACC CGGAGTTCCG
151  TCGTCTTGTT GAGCTTTATG CAAAGGATGA AGATGCATTC TTCAGAGACT
201  ACGCGGAATC GCACAAGAAA CTCTCTGAGC TTGGTTTCAA CCCAAACTCC
251  TCAGCAGGCA AGCAGTTGC AGACAGCACG ATTCTGGCAC AGAGTGCGTT
301  CGGGGTTGCA GTTGCTGCTG CGGTTGTGGC ATTTGGTTAC TTTTACGAGA
351  TTCGGAAGAG GATGAAGTAA ACGAAATAGG AAGGAAAACA CGAAGCAACG
401  ATGCTCTTAT TTGGGTATTA AAGAAACTAT TAATCGTCTA TCGAATCTAT
451  TTGCTGCTA CAAGATTCTA AACTCTTTGA ATCCACGATT CCACTGTTTA
501  GTAGTAAAAA AGTTAAAAAG TCAATATTTT GGGTCCGTGA TTCATTTTTG
551  CGATAAA
```

(SEQ ID NO: 17)

FIG. 6

```
  1 HPERSGFDGP WTQEPLKFDN SYFVELLKGE SEGLLKLPTD KTLLEDPEFR
 51 RLVELYAKDE DAFFRDYAES HKKLSELGFN PNSSAGKAVA DSTILAQSAF
101 GVAVAAAVVA FGYFYEIRKR MK*
```

(SEQ ID NO: 18)

FIG. 7

```
  1 GAGTGACGAA CATTGCGTGA AATTCTTGAA GAACTGCTAC GAGTCACTTC
 51 CAGAGGATGG AAAAGTGATA TTAGCAGAGT GTATTCTTCC AGAGACACCA
101 GACTCAAGCC TCTCAACCAA ACAAGTAGTC CATGTCGATT GCATTATGTT
151 GGCTCACAAT CCCGGAGGCA AGAACGAAC CGAGAAAGAG TTTGAGGCAT
201 TAGCCAAAGC ATCAGGCTTC AAGGGCATCA AGTTGTCTG CGACGCTTTT
251 GGTGTTAACC TTATTGAGTT ACTCAAGAAG CTCTAAAAAC AAACAATGTT
301 CCTATGAAGA TGATTTATAT GTAAACATTA TCTCATATCT CCTTCCACGG
351 TTCCAAAACT ATGCTGTTTA ATAATGGTTT TTACAAGAAT TGATTATGA
401 GTTTGTATTT TTGTTTGTTT GGAACAAAAT TATGTGATTA TAGGGAAAAA
451 TAAAATGAGC TATTATTGAA GAAAAAAA
```
(SEQ ID NO: 19)

FIG. 8

```
  1 SDEHCVKFLK NCYESLPEDG KVILAECILP ETPDSSLSTK QVVHVDCIML
 51 AHNPGGKERT EKEFEALAKA SGFKGIKVVC DAFGVNLIEL LKKL*
```

(SEQ ID NO: 20)

FIG. 9

```
   1  CCAGATTATC CCTCCCCCGA ATTCGGCACG AGGAAAAATC CTCTTCTTTC
  51  AGATGAGAAA CCCAAATCGA CGGAGGAGAA TAAGAGTTCT AAGCCGGAAT
 101  CAGCTTCTGG GAGTTCAACT TCATCAGCTA TGCCTGGCTT GAATTTCAAT
 151  GCTTTTGATT TCTCTAATAT GGCTAGTATT CTCAACGATC CTAGCATCAG
 201  AGAAATGGCT GAGCAAATAG CTAAAGATCC TGCCTTTAAC CAATTGGCTG
 251  AGCAGCTTCA GAGATCTATT CCTAACGCTG CCAGGAAGG TGGTTTCCCT
 301  AACTTTGATC CTCAACAGTA TGTCAATACA ATGCAACAGG TTATGCATAA
 351  CCCTGAGTTT AAGACAATGG CCGAGAAACT TGGTACCGCC TTAGTTCAGG
 401  ATCCACAAAT GTCTCCTTTT TTGGATGCTT TCTCGAATCC TGAAACAGCA
 451  GAACACTTTA CTGAGCGTAT GGCGCGGATG AAAGAAGATC CAGAGTTGAA
 501  ACCTATACTA GATGAGATTG ATGCTGGTGG TCCTTCTGCC ATGATGAAGT
 551  ACTGGAATGA TCCAGAAGTG CTGAAAAAGC TGGGTGAAGC AATGGGTATG
 601  CCTGTTGCTG GCTTACCAGA CCAGACTGTT TCAGCTGAAC CTGAGGTAGC
 651  AGAAGAAGGT GAAGAAGAAG AGTCTATTGT TCACCAAACT GCCAGTCTTG
 701  GTGATGTTGA GGGTTTGAAA GCTGCCTTGG CATCTGGTGG TAACAAAGAT
 751  GAAGAAGATT CTGAAGGAAG GACAGCATTG CATTTTGCTT GTGGATACGG
 801  CGAGTTGAAA TGTGCTCAAG TTCTTATCGA TGCTGGAGCA AGTGTTAATG
 851  CGGTTGACAA AAACAAGAAC ACACCTCTGC ATTATGCTGC TGGTTACGGG
 901  AGGAAAGAGA GTGTAAGCCT TCTCCTGGAG AATGGTGCTG CAGTCACTCT
 951  GCAAAACCTA GACGAGAAGA CGCCAATTGA TGTAGCGAAG CTCAACAGCC
1001  AGCTGGAGGT GGTGAAGCTG CTTGAGAAGG ATGCTTTCCT TGAGCTCTG
1051  CTGGTTAAAG GAAAGCTCTA AGCTCATATT GTCTTTGAGG CATTTGTCTT
1101  GTGTGTGTCC TGAACCAGTT TCACAGGCTT TTTGTGTACA CTTTTTATTA
1151  GTTCCTCTCT TCTTCTAAAT TTGTCTCTTA TGTTGTTTTA AAAGTCAATA
1201  AAGAAAGAAA TAGCAATCAA TGATTTAATT TATGATTATA TTCTTTATTT
1251  CGTCGACCTC TACAGAATGA TTCAATTTGG AAGAATCATT CTGGTTTGGA
1301  GGATATGTAA GAAAAACTAC TTGATCTCCA AGTTATTCCA TTCTTCTGTT
1351  GAAAAAA
```

(SEQ ID NO: 21)

FIG. 10

| | | | | |
|---|---|---|---|---|
| 1 GTRKNPLLSD | EKPKSTEENK | SSKPESASGS | STSSAMPGLN | FNAFDFSNMA |
| 51 SILNDPSIRE | MAEQIAKDPA | FNQLAEQLQR | SIPNAGQEGG | FPNFDPQQYV |
| 101 NTMQQVMHNP | EFKTMAEKLG | TALVQDPQMS | PFLDAFSNPE | TAEHFTERMA |
| 151 RMKEDPELKP | ILDEIDAGGP | SAMMKYWNDP | EVLKKLGEAM | GMPVAGLPDQ |
| 201 TVSAEPEVAE | EGEEEESIVH | QTASLGDVEG | LKAALASGGN | KDEEDSEGRT |
| 251 ALHFACGYGE | LKCAQVLIDA | GASVNAVDKN | KNTPLHYAAG | YGRKESVSLL |
| 301 LENGAAVTLQ | NLDEKTPIDV | AKLNSQLEVV | KLLEKDAFL* | |

(SEQ ID NO: 22)

FIG. 11

```
  1 TTTTAAAAAA TTTTGCCATC AACCGTAGAT GTTCCGCCAA AGGGTGGGTT
 51 TAGCTTCGAT CTGTGTAAGA GAAATGATAT TCTTACACAA AAGGGTCTTA
101 AAGCTCCGTC TTTTTTGAAG ACTGGAACAA CCATTGTTGG TTTGATTTTC
151 AAGGATGGTG TGATACAAGG GGCAGATACC CGAGCAACTG AGGGGCCAAT
201 TGTTGCTGAT AAGAACTGTG AGAAGATTCA CTATATGGCA CCAAACATAT
251 ATTGCTGTGG TGCAGGAACT CGGGCTGATA CTGAAGCAGT CACTGATATG
301 GTCAGCTCAC AGCTGCGATT GCATCGTTAC CAGACTGGTC GAGACTCTCG
351 GGTCATTACT GCTTTGACCC TTCTCAAAAA ACATTTTTTC AGCTACCAAG
401 GTCATGTCTC TGCTGCTCTT GTACTCGGTG GAGTTGATAT CACTGGTCCA
451 CATCTGCATA CTATATACCC ACACGGTTCA ACTGACACTC TTCCATTCGC
501 CACAATGGGT TCGGGTTCTC TTGCTGCTAT GTCTGTGTTT GAGGCAAAGT
551 ATAAAGAAGG CCTAACTAGG GATGAAGGAA TTAAGCTGGT CGCTGAATCC
601 ATATGCTCGG GTATATCCAA TGACCTGGGT AGTGGTAGCA ACGTGGACAT
651 CTGCGTGATC ACA
```

(SEQ ID NO: 23)

FIG. 12

```
KILPSTVD VPPKGGFSFD LCKRNDILTQ KGLKAPSFLK TGTTIVGLIF
KDGVIQGADT RATEGPIVAD KNCEKIHYMA PNIYCCGAGT RADTEAVTDM
VSSQLRLHRY QTGRDSRVIT ALTLLKKHFF SYQGHVSAAL VLGGVDITGP
HLHTIYPHGS TDTLPFATMG SGSLAAMSVF EAKYKEGLTR DEGIKLVAES
ICSGISNDLG SGSNVDICVI T
```

(SEQ ID NO: 24)

FIG. 13

```
  1  ACGAGAGGCC CTGAGACGCG GCAGATATCA GGTCCTGCGA CTTCAACACA
 51  GATCAGGAAC TTCACATTAT GTCAGCATCT GCAAGGAATC CACACACATA
101  TCTCATCCAT GGTAGCGGAC CTTCCCAGTA TTGCTACTGA TGTATTGTCT
151  CCTTATCTGG CTGCAATCTA TAATGCGGCA TGTGAGCCAG TTACACCTTT
201  GTTTAAAGCA ATGCGAGACA AGCTCGAGTC ATGCATTCTT CAAATCCATG
251  ATCAAAACTT TGGTGCTGAT GACGCTGACA TGGACAACAA CGCTTCCTCA
301  TACATGGAGG AGTTGCAGAG ATCGATTCTT CACTTCCGCA AGGAGTTCCT
351  ATCTAGACTA TTGCCTTCCG CAGCAAATGC TAACACTGCA GGAACAGAAT
401  CGATCTGCAC AAGACTCACA AGACAAATGG CGTCAAGGGT TTTGATCTTC
451  TACATCAGAC ATGCATCCCT TGTGCGACCA CTTTCAGAAT GGGGAAAACT
501  CAGAATGGCC AAAGACATGG CCGAGCTGGA ACTAGCAGTG GGACAGAATC
551  TATTTCCCGT GGAACAACTC GGAGCACCGT ACAGAGCTCT TAGAGCGTTT
601  AGGCCTTTGG TTTTCCTGGA AACATCTCAA ATGGGATCAT CTCCTCTCAT
651  CAATGATCTA CCACCGAGCA TCGTCCTACA TCATCTCTAC ACAAGAGGCC
701  CAGACGAGTT AGAGTCACCG ATGCAGAAGA ACAGACTAAG TCCTAAACAG
751  TACTCACTGT GGCTTGATAA CCAAAGAGAG GATCAGATCT GGAAAGGGAT
801  AAAAGCAACT TTGGATGATT ATGCAGTGAA GATCAGATCG AGAGGGGACA
851  AAGAGTTTAG TCCAGGTTAT CCTCTAATGC TTCAAATTGG TTCATCTTTA
901  ACACAAGAAA ACTTATAAGC TGTGCTTTGT TACCGAATCA ATATTCTTCT
951  ATTGCGAACT TTTTGTCTC AAAAAA
```

(SEQ ID NO: 25)

FIG. 14

```
  1  TRGPETRQIS GPATSTQIRN FTLCQHLQGI HTHISSMVAD LPSIATDVLS
 51  PYLAAIYNAA CEPVTPLFKA MRDKLESCIL QIHDQNFGAD DADMDNNASS
101  YMEELQRSIL HFRKEFLSRL LPSAANANTA GTESICTRLT RQMASRVLIF
151  YIRHASLVRP LSEWGKLRMA KDMAELELAV GQNLFPVEQL GAPYRALRAF
201  RPLVFLETSQ MGSSPLINDL PPSIVLHHLY TRGPDELESP MQKNRLSPKQ
251  YSLWLDNQRE DQIWKGIKAT LDDYAVKIRS RGDKEFSPGY PLMLQIGSSL
301  TQENL*
```

(SEQ ID NO: 26)

FIG. 15

CRUCIFER AFT PROTEINS AND USES THEREOF

BACKGROUND OF THE INVENTION

This invention relates to recombinant plant nucleic acids and polypeptides.

Improved means to manipulate plant gene expression is desired for a variety of industrial, agricultural, and commercial food uses. To produce new plant varieties, it is necessary to change the genetic makeup of the crop or plant in question. Desirable genes have to be incorporated into the crop or plant, and undesirable genes have to be eliminated or replaced. In other words, one needs to genetically engineer the plant to meet the demands of agriculture. Accordingly, genetic engineering of crop plants necessitates methods of identifying potentially valuable genes and transferring these to the crop that one desires to improve.

SUMMARY OF THE INVENTION

We have identified and describe herein a novel plant transcriptional activator from the crucifer, *Arabidopsis thaliana*. In addition to its role as a transcriptional activator, we have also determined that this protein plays a role in plant defense mechanisms by interacting with proteins, e.g., 3-O-methyltransferase and ascorbate peroxidase, involved in protecting plants from pathogens. We named this protein AFT1 (Arabidopsis Fourteen-Three-three 1) because it shows sequence homology to the widespread 14-3-3 protein family.

The AFT1 protein provides a means to enhance, control, modify or otherwise alter plant gene expression, e.g, as a transcription activator or as a chimeric transcriptional activator, or even to modulate events during plant cell-signalling processes, e.g., signal transduction events involved in plant defense responses to pathogens such as fungi, nematodes, insects, bacteria, and viruses. Of special interest are the nucleic acid sequences corresponding to not only other AFT1 proteins found in the plant kingdom, but also sequences corresponding to proteins which interact with AFT1 during plant signal transduction events, e.g., those pathways which operate during a plant's response to a pathogen, for applications in genetic engineering, especially as related to agricultural biotechnology.

Accordingly, in general, the invention features recombinant AFT1 polypeptides, preferably, including an amino acid sequence substantially identical to the amino acid sequence shown in FIG. 1 (SEQ ID NO: 2). The invention also features a recombinant polypeptide which is a fragment or analog of an AFT1 polypeptide that includes a domain capable of activating transcription, e.g., AFT1 (34-248)(SEQ ID NO: 27) or AFT1 (122-248)(SEQ ID NO: 28). Transcription activation may be assayed, for example, according to the methods described herein.

In various preferred embodiments, the polypeptide is derived from a plant (e.g., a monocot or dicot), and preferably from a crucifer such as Arabidopsis.

In a second aspect, the invention features a chimeric AFT1 transcriptional activation protein including an AFT1 polypeptide fused to a DNA-binding polypeptide. In preferred embodiments, the DNA-binding polypeptide includes, without limitation, Gal4 or LexA.

In a third aspect, the invention features a transgenic plant containing a transgene comprising an AFT1 protein operably linked to a constitutive (e.g., the 35S CaMV promoter) or regulated or inducible promoter (e.g., rbcS promoter). In other related aspects, the invention also features a transgenic plant containing a transgene containing a chimeric AFT1 transcriptional activator protein. In related aspects, the invention features a seed and a cell from a transgenic plant containing the AFT1 protein, fragment or analog, or a chimeric AFT1 transcriptional activator protein.

In a fourth aspect, the invention features a transgenic plant expressing a polypeptide of interest which involves: (a) a nucleic acid sequence encoding a chimeric AFT1 transcriptional activator protein; and (b) a nucleic acid sequence encoding a polypeptide of interest in an expressible genetic construction, wherein the binding of the chimeric protein regulates the expression of the polypeptide of interest. In preferred embodiments the polypeptide of interest is, without limitation, a storage protein, e.g., napin, legumin, or phaseolin, or any other protein of agricultural significance.

In a fifth aspect, the invention features substantially pure DNA (for example, genomic DNA, cDNA, or synthetic DNA) encoding an AFT1 protein. Accordingly, the invention features a nucleotide sequence substantially identical to the nucleotide sequence shown in FIG. 1 (SEQ ID NO: 1). In related aspects, the invention also features substantially pure DNA encoding a recombinant polypeptide including an amino acid sequence substantially identical to the amino acid sequence of AFT1 polypeptide shown in FIG. 1 (SEQ ID NO: 2). Such DNA may, if desired, be operably linked to a constitutive or regulated or inducible promoter as described herein. In preferred embodiments, the DNA sequence is from a crucifer (e.g., Arabidopsis). In related aspects, the invention also features a vector, a cell (e.g., a plant cell), and a transgenic plant or seed thereof which includes such substantially pure AFT1 DNA. In various preferred embodiments, the cell is a prokaryotic cell, for example, E. coli or Agrobacterium, or more preferably, a eukaryotic cell, for example, a transformed plant cell derived from a cell of a transgenic plant.

In a sixth aspect, the invention features a recombinant polypeptide which is a fragment or analog of an AFT1 polypeptide (SEQ ID NO: 2) including a domain capable of interacting with a plant defense related protein. Preferably, the polypeptide is AFT1(33-194)(SEQ ID NO: 29). In related aspects, the invention also features substantially pure DNA encoding an AFT1 polypeptide fragment or analog, preferably the DNA is substantially identical to the DNA sequence shown in FIG. 1 (SEQ ID NO: 1). In other aspects, the DNA is operably linked to a constitutive or regulated or inducible promoter.

By "crucifer" is meant any plant that is classified within the Cruciferae family as commonly described in, e.g., Gray's Manual of Botany American Book Company, N.Y., 1950; *Hortus Third: A Concise Dictionary of Plants Cultivated in the U.S. and Canada*, Macmillan, 1976; or Simmons, N.W., *Evolution of Crop Plants*, 1986. The Cruciferae include many agricultural crops, including, broccoli, cabbage, brussel sprouts, rapeseed, kale, Chinese kale, cauliflower, horseradish, and Arabidopsis.

By "AFT1" is meant a crucifer polypeptide capable of effecting transcriptional activation or interacting with a polypeptide involved with a plant defense polypeptide. Such an AFT1 polypeptide has the sequence shown in FIG. 1 (SEQ ID NO.: 1).

By "protein" and "polypeptide" is meant any chain of amino acids, regardless of length or post-translational modification (e.g., glycosylation or phosphorylation).

By "substantially identical" is meant a polypeptide or nucleic acid exhibiting at least 90%, preferably 93%, more preferably 95%, and most preferably 97% homology to a reference amino acid or nucleic acid sequence. For polypeptides, the length of comparison sequences will generally be at least 16 amino acids, preferably at least 20 amino acids, more preferably at least 25 amino acids, and most preferably 35 amino acids. For nucleic acids, the length of comparison sequences will generally be at least 50 nucleotides, preferably at least 60 nucleotides, more preferably at least 75 nucleotides, and most preferably 110 nucleotides.

Homology is typically measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various substitutions, deletions, substitutions, and other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

By a "substantially pure polypeptide" is meant an AFT1 protein which has been separated from components which naturally accompany it. Typically, the polypeptide is substantially pure when it is at least 60%, by weight, free from the proteins and naturally-occurring organic molecules with which it is naturally associated. Preferably, the preparation is at least 75%, more preferably at least 90%, and most preferably at least 99%, by weight, AFT1 polypeptide. A substantially pure AFT1 polypeptide may be obtained, for example, by extraction from a natural source (e.g., a plant cell); by expression of a recombinant nucleic acid encoding an AFT1 polypeptide; or by chemically synthesizing the protein. Purity can be measured by any appropriate method, e.g., those described in column chromatography, polyacrylamide gel electrophoresis, or by HPLC analysis.

A protein is substantially free of naturally associated components when it is separated from those contaminants which accompany it in its natural state. Thus, a protein which is chemically synthesized or produced in a cellular system different from the cell from which it naturally originates will be substantially free from its naturally associated components. Accordingly, substantially pure polypeptides include those derived from eukaryotic organisms but synthesized in *E. coli* or other prokaryotes.

By "substantially pure DNA" is meant DNA that is free of the genes which, in the naturally-occurring genome of the organism from which the DNA of the invention is derived, flank the gene. The term therefore includes, for example, a recombinant DNA which is incorporated into a vector; into an autonomously replicating plasmid or virus; or into the genomic DNA of a prokaryote or eukaryote; or which exists as a separate molecule (e.g., a cDNA or a genomic or cDNA fragment produced by PCR or restriction endonuclease digestion) independent of other sequences. It also includes a recombinant DNA which is part of a hybrid gene encoding additional polypeptide sequence.

By "transformed cell" is meant a cell into which (or into an ancestor of which) has been introduced, by means of recombinant DNA techniques, a DNA molecule encoding (as used herein) an AFT1 protein or an AFT1 chimeric transcriptional activator.

By "promoter" is meant a DNA sequence sufficient to direct transcription; such elements may be located in the 5' or 3' regions of the gene. By "constitutive" promoter is meant a promoter capable of mediating gene expression without regulation, i.e., the promoter is always transcriptionally active. By "regulated or inducible" promoter is meant a promoter capable of mediating gene expression in response to a variety of developmental (e.g., cell-specific, tissue-specific, and organ-specific promoters), environmental, and hormonal cues including, but not limited to, promoters such as the rbcS, wunI, chlorophyll a/b, or $E_2$ promoters described herein.

By "operably linked" is meant that a gene and a regulatory sequence(s) (e.g., a promoter) are connected in such a way as to permit gene expression when the appropriate molecules (e.g., transcriptional activator proteins) are bound to the regulatory sequence(s).

By "plant cell" is meant any self-propagating cell bounded by a semi-permeable membrane and containing a plastid. Such a cell also requires a cell wall if further propagation is desired. Plant cell, as used herein includes, without limitation, algae, cyanobacteria, seeds suspension cultures, embryos, meristematic regions, callus tissue, leaves, roots, shoots, gametophytes, sporophytes, pollen, and microspores.

By "transgene" is meant any piece of DNA which is inserted by artifice into a cell, and becomes part of the genome of the organism which develops from that cell. Such a transgene may include a gene which is partly or entirely heterologous (i.e., foreign) to the transgenic organism, or may represent a gene homologous to an endogenous gene of the organism.

By "transgenic" is meant any cell which includes a DNA sequence which is inserted by artifice into a cell and becomes part of the genome of the organism which develops from that cell. As used herein, the transgenic organisms are generally transgenic plants and the DNA (transgene) is inserted by artifice into either the nuclear or plastidic genome.

By "plant defense related protein" is meant any protein which is involved in the protection or resistance to plant pests (e.g., bacteria, insects, nematodes, fungi, and viruses). Such proteins include, without limitation, 3-O-methyltransferases, ascorbate peroxidases, chalcone synthases, hydroxyproline rich glycoproteins, glucanases, chitanases, and proteinase inhibitors.

Other features and advantages of the invention will be apparent from the following description of the preferred embodiments thereof, and from the claims.

DETAILED DESCRIPTION

The drawings will first be briefly described.

Drawings FIG. 1 is the nucleic acid sequence (SEQ ID NO: 1) and deduced amino acid sequence of Arabidopsis AFT1 (SEQ ID NO: 2).

FIG. 2 shows the LexA-dependent activation of LEU2 expression by AFT1; activation was monitored by the growth of yeast on a leucine-minus plate. The AFT1 clone in vector pJG4-5 which directs the production of AFT1/B42 fusion protein was introduced into the yeast strain EGY48 where different plasmids had already been introduced. The plasmids which either direct production of different LexA fusion proteins or no LexA protein are pEG202 (LexA alone, a), pHM1-1 (LexA/Biocoid, b), pHM12 (LexA/Cdc2, c), pHM7-3 (LexA/Ftz homeo-domain), d), pAKR1-261 (LexA/AKR1-261), e), pAKR249-434 (LexA/AKR249-434, f), pAKR114-434 (LexA/AKR114-434, g), and pHM, (no LexA, h).

FIGS. 3A–B are a schematic representation showing transcription activation by AFT1. The effects of various fusion proteins were monitored by the growth of yeast in the absence of leucine and quantitated by measuring the activity of the β-galactosidase. Panel (A) shows transcription activation by AFT1 and its derivatives fused to the activation domain B42 upon introduction into the yeast strain EGY48. This strain also contains the plasmid pEG202 which directs constitutive production of LexA protein and plasmid pSH18-34 which contains the reporter gene LexAop-LacZ. Panel (B) shows transcription activation by AFT1 and its derivatives fused to the LexA protein in the plasmid pEG202 upon introduction into the yeast strain EGY48 containing the/plasmid pSH18-34 only.

FIG. 4 shows a genomic Southern blot analysis. The blot was probed with a labeled AFT1 cDNA clone. The lanes labeled C contain Columbia DNA and L, Landsberg DNA. The restriction enzymes used are indicated above the lanes. The sizes of λ-Hind III digested DNA fragments used as length markers are show on the left.

FIGS. 5A–C shows a RNA blot analysis of AFT1 expression. Panel (A) shows the developmental expression of AFT1. RNAs were extracted from greenhouse-grown plants; Panel (B) shows the organ-specific expression of AFT1. RNAs of leaf, root, and stem were extracted from plate-grown plants, and RNAs of flower and silique were extracted from greenhouse-grown plants. Panel (C) shows the effect of light on the expression of Lhca2 and AFT1. RNAs were extracted from greenhouse-grown plants.

FIG. 6 shows the DNA sequence (SEQ ID NO: 17) of an isolated cDNA found to be an AFT1 interacting protein coding for ascorbate peroxidase.

FIG. 7 shows the partial amino acid sequence (SEQ ID NO: 18) of ascorbate peroxidase deduced from the isolated cDNA (SEQ ID NO: 17).

FIG. 8 shows the DNA sequence (SEQ ID NO: 19) of an isolated cDNA found to be an AFT1 interacting protein coding for 3-O-methyltansferase.

FIG. 9 shows the partial amino acid sequence (SEQ ID NO: 20) of 3-O-methyltransferase deduced from the isolated cDNA (SEQ ID NO: 19).

FIG. 10 shows the DNA sequence (SEQ ID NO: 21) of an isolated cDNA found to be an AFT1 interacting protein coding for an Arabidopsis ankryin repeating protein $AKR_2$.

FIG. 11 shows the partial amino acid sequence (SEQ ID NO: 22) of an Arabidopsis ankryin repeating protein $AKR_2$ deduced from the isolated cDNA (SEQ ID NO: 21).

FIG. 12 shows the DNA sequence (SEQ ID NO: 23) of an isolated cDNA found to be an AFT1 interacting protein coding for proteasome.

FIG. 13 shows the partial amino acid sequence (SEQ ID NO: 24) of proteasome deduced from the isolated cDNA (SEQ ID NO: 23).

FIG. 14 shows the DNA sequence (SEQ ID NO: 25) of an isolated cDNA found to be an AFT1 interacting protein.

FIG. 15 shows the partial amino acid sequence (SEQ ID NO: 26) deduced from the isolated cDNA (SEQ ID NO: 25).

POLYPETIDES ACCORDING TO THE INVENTION

Polypeptides according to the invention include the entire Arabidopsis AFT1 protein (as described in FIG. 1; SEQ ID No: 2). These polypeptides are used, e.g., to manipulate plant gene expression at the transcriptional level (as discussed infra) or to manipulate the plant signal transduction pathway by providing plants with the potential of resisting pathogens such as fungi, insects, nematodes, bacteria, and viruses. Polypeptides of the invention also include any analog or fragment of the Arabidopsis AFT1 protein capable of activating transcription in a host plant. The efficacy of an AFT1 analog or fragment to activate transcription is dependent upon its ability to interact with the transcription complex; such an interaction may be readily assayed using any number of standard in vivo methods, e.g., the interaction trap mechanism described infra. Similarly, the polypeptides of the invention include chimeric AFT1 transcriptional activator proteins capable of selectively activating transcription of a specified gene.

Specific AFT1 analogs of interest include full-length or partial (described infra) AFT1 proteins, including amino acid sequences which differ only by conservative amino acid substitutions, for example, substitutions of one amino acid for another of the same class (e.g., valine for glycine, arginine for lysine, etc.) or by one or more non-conservative amino acid substitutions, deletions, or insertions at positions of the amino acid sequence which will not destroy AFT1's ability to activate transcription (e.g., as assayed infra).

Specific AFT1 fragments of interest include any portions of the AFT1 protein which are capable of interaction with an AFT1 ligand, e.g., a member of the transcriptional complex or a protein involved in plant defense mechanisms, such as 3-O-methyltransferase, and ascorbate peroxidase. Identification of such ligands may be readily assayed using any number of standard in vivo methods, e.g., the interaction trap mechanism described infra.

There now follows a description of the cloning and characterization of an Arabidopsis AFT-encoding cDNA useful in the instant invention, and a characterization of its ability to activate transcription, and its protein interacting properties. This example is provided for the purpose of illustrating the invention and should not be construed as limiting.

Isolation of an Arabidopsis Gene Encodidng an AFT Protein

The Arabidopsis AFT1 gene was isolated as follows. A yeast interaction trap system (Zervos et al., Cell 72: 223–232, 1993; Gyuris et al., Cell 75: 791–803, 1993) was modified for the isolation of an Arabidopsis AFT protein. The yeast strain EGY48 (MATa trp1 ura3 his3 LEU2::plexAop6-LEU2) containing a plasmid pJK103 (Zervos et al., supra) that directs expression of a Gall-lacZ gene from two high affinity ColE1 LexA operators, was used in the interaction trap experiment. A "bait" (LexA/AKR1-261, residues 1-261 of AKRP (Arabidopsis anKyrin repeat protein) fused to DNA binding protein LexA) was introduced into the strain and then an Arabidopsis cDNA expression library was introduced (see, e.g., Zhang et al., Plant Cell 4: 1575–1588, 1992). Selection was first carried out on leucine minus plates, and Leu$^+$ colonies were analyzed on X-gal plates. The clones which activated transcription of reporter genes in the presence of, but not in the absence of, the LexA protein or its fusion derivatives were isolated.

The oligo(dT)-primed activation-tagged cDNA expression library in vector pJG4-5 (Gyuris et al., supra) was made from mRNA of four week-old Arabidopsis leaves. The yeast strain EGY48, the vector plasmids pJG4-5 and pEG202, and the plasmids pHM1—1, pHM7-3, pHM12, pHMø, and pSH18-34 were provided by Dr. Roger Brent. The LexA/

AKR fusion proteins were constructed as follows. The oligonucleotides used to amplify desired AKR fragments which were later subcloned into pEG202 are shown below.

| | | |
|---|---|---|
| OAB-9: | GCGGAATTCATGAGGCCCATTAAAATT | (SEQ ID NO: 3) |
| OAB-10: | GTAGGATCCGGTCGGATTTCTTGTCGC | (SEQ ID NO: 4) |
| OAB-11: | CGCGAATTCAATAGCGACAAGTACGAT | (SEQ ID NO: 5) |
| OAB-12: | GTAGGATCCGTCTCTCTTCCAAGGTAGA | (SEQ ID NO: 6) |
| OAB-20: | GATCCTAGAATTCAAGAAGAATCGGCGTGGC | (SEQ ID NO: 7) |

The combination of oligonucleotides used for fusion proteins are: OAB-9 and OAB-10 (LexA/AKR1-261); OAB-11 and OAB-12 (LexA/AKR249-434); OAB-20 and OAB-12 (LexA/AKR114-434). Normally, with this technique, a library that expresses cDNA-encoded proteins fused to a transcription activator domain (B42) is introduced into a special yeast strain. This strain also contains a plasmid which directs constitutive production of a transcriptionally inert LexA fusion protein which is called the "bait" (LexA fused to the protein of interest) and two reporter genes. The transcription of these two reporter genes can be stimulated if the cDNA-encoded protein complexes with the bait. One reporter gene LEU2 allows growth in the absence of leucine and the other reporter gene LacZ codes for β-galactosidase.

We found that many proteins encoded by Arabidopsis cDNAs activated transcription with LexA protein alone, or with many different baits, although all of these proteins required a LexA binding domain. This results in the isolation of cDNA clones which are not true interaction partners of the "bait" and requires further analysis to separate these "false positive" clones from the desired partner clones. Examples of activation by AFT1 which is dependent upon the presence of LexA are shown in FIG. 2. To further understand such activation, we characterized 81 cDNA clones which encoded proteins capable of activating the expression of the reporter genes. Among the cDNAs sequenced, 36 clones were derived from the same gene which encodes a 14-3-3-like protein. This gene was named AFT1 (Arabidopsis Fourteen-Three-three 1), and the protein AFT1 encodes is designated as AFT1. AFT1 contains 248 amino acids with a molecular weight of about 28 kD.

Transcription Activation by AFT1

A series of experiments were performed to determine which AFT1 sequences were required for transcriptional activation in the yeast interaction trap system. Accordingly, a series of deletion constructs were made and analyzed according to methods known in the art as follows. To test activation by B42/AFT1 fusion proteins, a series of AFT1 derivatives fused to B42 in the plasmid pJG4-5 were constructed. These plasmids were introduced into the strain EGY48 containing the plasmid pEG202 which directs the constitutive production of LexA protein and the plasmid pSH18-34 which contains the LexAop-LacZ reporter gene.

To test activation by LexA/AFT1 fusion proteins, a series of AFT1 derivatives were fused to LexA in the plasmid pEG202 were constructed and were introduced into the strain EGY48 containing the plasmid pSH18-34. Transcription activation by AFT1 and its derivatives was measured by the growth of yeast on leucine minus plates and the activity of β-galactosidase. The assay for β-galactosidase was conducted as described by Zervos et al., supra. The oligonucleotides used to amplify desired AFT1 fragments which were later subcloned into pJG4-5 and pEG202 are shown below.

| | | |
|---|---|---|
| JW-5: | CTGACTGAATTCATGGCGGCGACATTAGG | (SEQ ID NO: 8) |
| JW-6: | GACTGAGTCGACCCTTCATCTAGATCCTC | (SEQ ID NO: 9) |
| JW-7: | GACTGACTCGAGCCTTCATCTAGATCCTCA | (SEQ ID NO: 10) |
| JW-8: | CTGACTGAATTCGAGTCTAAGGTCTTTAC | (SEQ ID NO: 11) |
| JW-9: | GACTGACTCGAGACTCGCTCCAGCAGATGG | (SEQ ID NO: 12) |
| JW-10: | GACTGACTCGAGTGAAGAATTGAGAATCTC | (SEQ ID NO: 13) |
| JW-11: | GACTGAGTCGACACTCGCTCCAGCAGATGG | (SEQ ID NO: 14) |
| JW-12: | GACTGAGTCGACTGAAGAATTGAGAATCTC | (SEQ ID NO: 15) |
| JW-13: | CTGACTGAATTCGTTACAGGCGCTACTCCAG | (SEQ ID NO: 16) |

The combinations of oligonucleotides used for fusion proteins were: JW-5 and JW-6 (LexA/1-248); JW-5 and JW-12 (LexA/1-194); JW-5 and JW-11 (LexA/1-121); JW-13 and JW-6 (LexA/34-248); JW-8 and JW-6 (LexA/122-248); JW-5 and JW-7 (B42/1-248); JW-5 and JW-9 (B42/1-121); JW-13 and JW-7 (B42/34-248); JW-8 and JW-7 (B42/122-248); JW-13 and JW-10 (B42/34-194).

Results from such experiments revealed that deletion of the C-terminal half of AFT1 (B42/1-121) completely abolished AFT1's ability to activate, whereas deletion of either 33 or 121 residues from the N-terminus (B42/34-248 and B42/122-248) increased activation (FIG. 3A). The reason for the increased activation is not known, but might be due to the tertiary structures of these two fusion proteins (B42/34-248 and B42/122-248) which could result in stronger interactions with the transcriptional machinery. Nevertheless, it is the C-terminal half that is responsible for the observed activation when AFT1 is fused to B42, e.g., AFT1 residues 34–248 (SEQ ID NO: 27) and 122–248 (SEQ ID NO: 28). However, since B42 is an activator domain, the observed transcription activation may be due to the direct interaction of AFT1 with LexA, thereby bringing B42 into the proximity of the reporter gene promoter. An alternate possibility is suggested by the acidic nature of AFT1 (pI=4.6), namely, AFT1 itself might be a transcription activator, since it shares this acidic feature with many transcription activators.

AFT1 was also fused directly to LexA to test if AFT1 can activate transcription. The results shown in FIG. 3B demonstrate that AFT1 does activate transcription. To determine which portion of AFT1 was important for activation, 54 amino acids were deleted from the AFT C-terminus (LexA/1-194). This deletion caused AFT1 to lose its ability to activate completely; whereas deletion of 33 amino acids from the N-terminus, (LexA/34-248) decreased activation by about 75%. As shown in Panel B of FIG. 3, when the N-terminal half of AFT1 (LexA/122-248) was deleted, activation dropped to basal levels. Thus, even though the C-terminal half is critical for activation and is more acidic than the N-terminal half, the N-terminal half also plays a role in activation.

AFT1 Copy Number

The copy number of the AFT1 gene was determined by genomic DNA (Southern) blot analysis. Genomic DNA was prepared according to the method of Dellaporta et al. (Plant Mol. Biol. Rep. 4: 19–21, 1983), digested with restriction enzymes, electrophoresed (5 μg per lane), blotted to a Biotrans™ Nylon membrane, and hybridized with labeled ATF1 cDNA clone. Hybridizations were carried out according to the method of Church and Gilbert (Proc. Natl. Acad. Sci. USA 81: 1991–1995, 1984) using probes labeled by random priming. The washing conditions were as follows: two times (10 minutes each) in 0.5% BSA, 1 mM EDTA, 40 mM NaHPO4 (pH 7.2), and 5.0% SDS at 63° C.; then four times (5 minutes each) in 1 mM EDTA, 40 mM NaHPO4 (pH 7.2), and 1% SDS at 63° C. The condition for deprobing filters was as follows: two times (15 minutes each) in 2 mM Tris (pH 8.2), 2 mM EDTA (pH 8.0), and 0.1% SDS at 70° C. for DNA blots and at 80° C. for RNA blots.

As shown in FIG. 4, digestion of two ecotypes (Columbia and Landsberg) of Arabidopsis DNA with the enzymes, Bgl II and Hind III, gave rise to two bands after the DNA blot was probed with a labelled AFT1 cDNA sequence. These data indicate that only one copy of AFT1 was present in both ecotypes of Arabidopsis, since there was one restriction site for Bgl II and one site for Hind III within the AFT1 cDNA, respectively.

Developmental Expression Pattern of the AFT1 Gene in Arabidopsis

The developmental and organ-specific expression of AFT1, as well as the light regulation of AFT1 expression, were studied by RNA (Northern blot) analysis. Total RNA was isolated according to the method of Logemann et al. (Anal. Biochem. 163: 16–20, 1987), separated by electrophoresis (15 μg per lane), blotted to a Biotrans™ Nylon membrane, and hybridized to the labeled AFT1 cDNA clone and the Arabidopsis Lhca2 cDNA clone. The conditions for hybridization and washing were the same as described in genomic Southern analysis supra. RNAs were extracted from Arabidopsis grown either in a greenhouse (16 hr light/8 hr dark at 25°±5° C.) or on agarose plates in a tissue culture room (16 hr light/8 hr dark at 20°±2° C.). Greenhouse-grown plants were used for developmental expression analyses. Leaves were harvested weekly for RNA preparation. Greenhouse-grown plants were also used for light induction experiments. At four weeks, plants were moved to a dark chamber for three days, then shifted back to light. Leaves were then harvested every two hours. Tissue culture-grown plants were used for organ-specific expression analyses. Leaf, root, and stem mRNAs were isolated from plants grown for 35 days on agarose plate in MS media supplemented with 1% sucrose, and the flower and silique mRNAs were isolated from plants grown for 35 days in the greenhouse. The MS was purchased from Sigma (Cat# M-0153). As shown in FIG. 5, Panel A and Table I, when total RNAs isolated from leaves of one to five week-old plants were hybridized to a labelled AFT1 cDNA, the steady-state m/RNA level of AFT1 did not change significantly over a five week period.

When RNAs isolated from different organs were analyzed, the steady-state mRNA level in silique was found to be about one fifth of that in flower, whereas the mRNA levels in leaves, roots, and stems were about the same (FIG. 5, Panel B; Table I). It should be noted that the mRNA levels from flowers and siliques are not directly comparable to those from leaves, roots, and stems (FIG. 5, Panel B), because they were from materials grown under different conditions (as described supra). However, the steady-state mRNA levels of flower and silique can be compared to that of five-week-old leaves shown in FIG. 5, Panel A. The quantitative data indicate that the AFT1 mRNA level in leaves is about two times higher than that in flowers and nine times higher than that in siliques (Table I, infra). The growth conditions can affect the steady-state mRNA level since greenhouse-grown plants contained three times more AFT1 mRNA than plate-grown plants (FIGS. 5, Panels A and B; Table I, infra). These data indicate that although AFT1 expression is probably required throughout much of the Arabidopsis life cycle, its steady-state mRNA level is still regulated organ-specifically. Furthermore, dark-adapted plants contain at least two times more steady-state mRNA than plants grown in light (FIG. 5, Panel C, Table I, infra), suggesting that light plays a role in the down-regulation of AFT1 expression.

The relative intensities of AFT1 mRNA derived from the data in FIG. 5 are shown below in Table I. The relative intensity data were collected from β-scanning of RNA gel blots by a Blot Analyzer, and normalized using the intensity of the 18s RNA band.

TABLE I

| A. Developmental Expression[a] | | | | | |
|---|---|---|---|---|---|
| Time (in weeks): | One | Two | Three | Four | Five |
| Relative Intensity of AFT1: | 41 | 45 | 58 | 38 | 36 |
| B. Organ-specific Expression[b] | | | | | |
| Organs: | Leaf | Root | Stem | Flower | Silique |
| Relative Intensity of AFT1: | 11 | 11 | 12 | 19 | 4 |
| C. Light Regulation[c] | | | | | |
| Time (in hours): | Zero | Two | Four | Six | Eight | Ten |
| Relative Intensity of Lhca2: | 0.2 | 0.24 | 1.6 | 3.2 | 3.9 | 6.5 |
| Relative Intensity of AFT1: | 132 | 49 | 39 | 34 | 38 | 44 |

[a] and [c]: RNAs from greenhouse-grown plants;
[b]: RNAs of leaf, root, and stem from plate-grown plants, RNAs of flower and silique from greenhouse-grown plants.

We have shown that the AFT1 gene of Arabidopsis encodes a novel protein which can activate transcription in yeast. Accordingly, we conclude that AFT1 functions as a transcriptional activator.

Chimeric AFT1 Proteins as Targeted Transcriptional Activators

Since plant gene expression varies in accordance with developmental stages of different cell types and in response to different environmental factors and hormonal cues, the proteins (including the gene regulatory sequences) of the present invention are most useful for applications aimed at improving or engineering plant varieties of agricultural or commercial interest.

Accordingly, the invention, in general terms, also involves the construction of and use of novel chimeric AFT1 proteins capable of selectively activating transcription of a specified gene, e.g., a crucifer storage protein such as napin. Targeted transcription of a gene is acquired by imbuing the AFT1 transcriptional activator with the ability to selectively activate a specific gene by fusing it to a DNA-binding domain which is capable of binding to the 5' upstream regulatory region, e.g., in the vicinity of the transcription start site. Such chimeric proteins contain two parts: the AFT1 transcriptional activation region (described supra) and a DNA binding domain that is directed to or specific for the transcriptional initiation region of interest. For example, a chimeric AFT1 transcriptional activator protein may be produced by fusing a Gal4 DNA binding region (see, e.g., Ma et al. Nature, 334: 631–633, 1988; Ma et al. Cell 48: 847–853, 1988) to the transcriptional activating portion of AFT1 according to methods known in the art (e.g., see Sadowski et al., Nature 335: 563–564, 1988).

Importantly, the gene of interest, e.g., a napin storage protein gene, placed under the transcriptional control of an AFT1 chimeric activator must include the appropriate DNA recognition sequence in its 5' upstream region. For example, to activate napin gene expression with a Gal4-AFT1 protein, the napin gene should contain a 5' GAL4 upstream activation sequence (UAS). Construction of such clones is well known in the art and is discussed infra. Moreover, those skilled in the art will easily recognize that the DNA binding domain component of the chimeric activator protein may be derived from any appropriate eukaryotic or prokaryotic source. Thus, fusion genes encoding chimeric AFT1 transcriptional activator proteins can be constructed which include virtually any DNA binding domain and the AFT1 transcriptional activator provided that the gene placed under the transcriptional control of the AFT1 chimeric activator contains the requisite DNA regulatory sequences which facilitates its binding. Such chimeric AFT1 transcriptional activator proteins are capable of activating transcription efficiently in transgenic plants (plasmid construction discussed infr). Furthermore, cells expressing such chimeric AFT1 transcriptional activator proteins, e.g., AFT1/Gal4, are capable of specifically activating and overexpressing the desired gene product.

To identify effective chimeric AFT1 transcriptional activator proteins in vivo or in vitro, functional analyses are performed. Such assays may be carried out using transiently transformed plant cells or transgenic plants harboring the appropriate transgenes, e.g., an AFT1/Gal4 transcriptional activator and a storage protein promoter region containing the requisite Gal4 DNA binding sequences, according to standard methods (see, e.g., Gelvin et al., supra).

To identify particularly useful combinations, i.e., chimeric AFT1 activators and its cognate genes, plasmids are constructed and analyzed in either transient assays or in vivo in transgenic plants. Construction of chimeric transgenes is by standard methods (see, e.g., Ausubel et al, supra). The wild-type promoter of a specific gene, e.g., the crucifer napin storage protein, containing the regulatory region the appropriate DNA-binding sequence, e.g., Gal4, is fused to a reporter gene, for example, the β-glucuronidase gene (GUS) (see, e.g., Jefferson, Plant. Mol. Biol. Rep. 316: 387, 1987) in a plant expression vector and introduced into a host by any established method (as described infra) along with the cognate AFT1 chimeric transcriptional activator expression construct. By "reporter gene" is meant a gene whose expression may be assayed; such genes include, without limitation, β-glucuronidase (GUS), luciferase, chloramphenicol transacetylase (CAT), and β-galactosidase. In one particular example, the expression vector is transformed into Agrobacterium followed by transformation of the plant material, e.g., leaf discs (see, e.g., Gelvin et al. infra). Regenerated shoots are selected on medium containing, e.g., kanamycin. After rooting, transgenic plantlets are transferred to soil and grown in a growth room.

Primary transformants are then assayed for chimeric AFT1-induced GUS activity either by quantitating GUS activity or by histochemical staining as described below. Untransformed plants are taken as controls.

Fluorometric analysis of GUS activity can be performed in any plant cell protoplast or transgenic plant according to standard methodologies. Alternatively, preparations of crude plant extracts can be assayed as described, e.g., by Jefferson (supra), using extracts standardized for protein concentration (see, e.g., Bradford, Anal. Biochem. 72: 248, 1976). GUS levels in different plant tissues are assayed by enzymatic conversion of 4-methylumbelliferyl glucuronide to 4-methylumbelliferone, which is quantified with a fluorimeter (e.g., Perkin-Elmer LS 2B, Norwalk, Conn.). Typically, the fluorimeter is set at 455 nm emission and 365 nm excitation wavelengths. GUS activity is generally expressed as picomoles per milligram of protein per minute (see, e.g., Jefferson supra).

Alternatively, GUS activity can be assayed by in situ histochemical staining, e.g., as follows. Whole tissues and thin sections from transgenic plants and untransformed control plant tissue can be stained by incubation with 5-bromo-4-chloro-3-indoyl β-D-glucuronic acid (X-gluc; Research Organics, Inc., Cleveland Ohio) as described by Jefferson et al (EMBO J 6: 3901, 1987) and Gallagher (GUS Protocols, 1992). Tissue sections are incubated at 37° C. in 2 mM X-gluc in 0.1M $NaPO_4$ (pH 7.0), and then sectioned. GUS activity in a transformed plant is easily identified by the presence of an indigo blue precipitate within the cells expressing the reporter gene. Stained material is optionally examined microscopically using bright-field and dark-field optics.

AFT1 Interacting Proteins

Other properties of the AFT1 protein can be explored by modifying the interaction trap system described supra. For example, proteins which interact with AFT1 can be isolated and identified. To this end, we used a LexA and partial AFT1 fusion protein as a bait (LexA/AFT1 33-194, i.e., AFT1 residues 33–194 (SEQ ID NO: 29) fused to LexA) to search for proteins capable of interacting with AFT1. We identified five novel cDNAs showing sequence homology to several plant genes, including plant defense related gene products, e.g., 3-O-methyltransferase (see, e.g., Poeydomenge et al. Plant Physiol. 105: 749–750, 1994 and Jaek et al., Mol. Plant-Microbe Interactions 5: 294–300, 1992) and ascorbate peroxidase (see, e.g., Mittler et al., Plant J. 5: 397–405, 1994; Mehdy, Plant Physiol. 105: 467–472, 1994), the proteasome gene product (see, e.g., Haffter et al., Nucleic Acids Res. 19: 5075, 1991), and an ankryin repeating protein gene product, $AKR_2$. The nucleotide sequences for these cDNAs are shown in FIGS. 6 (SEQ ID NO: 17), 8 (SEQ ID NO: 19), 10 (SEQ ID NO: 21), 12 (SEQ ID NO: 23), and 14 (SEQ ID NO: 25). The deduced amino acid sequences coded for by these cDNAs are shown in FIGS. 7 (SEQ ID NO: 18), 9 (SEQ ID NO: 20), 11 (SEQ ID NO: 22), 13 (SEQ ID NO: 24), and 15 (SEQ ID NO: 26).

AFT1 Polypeptide Expression

Polypeptides according to the invention may be produced by transformation of a suitable host cell with all or part of an AFT1 cDNA (e.g., the cDNA described above) in a suitable expression vehicle or with a plasmid construct designed to express the chimeric AFT1 transcriptional activator protein supra.

Those skilled in the field of molecular biology will understand that any of a wide variety of expression systems may be used to provide the recombinant protein. The precise host cell used is not critical to the invention. The AFT1 protein or chimeric activator protein may be produced in a prokaryotic host, e.g., *E. coli*, or in a eukaryotic host, e.g., *Saccharomyces cerevisiae*, mammalian cells (e.g., COS 1 or NIH 3T3 cells), or any of a number of plant cells including, without limitation, algae, tree species, ornamental species, temperate fruit species, tropical fruit species, vegetable species, legume species, monocots, dicots, or in any plant of commercial or agricultural significance. Particular examples of suitable plant hosts include Chlamydomonas, Conifers, Petunia, Tomato, Potato, Tobacco, Arabidopsis, Lettuce, Sunflower, Oilseed rape, Flax, Cotton, Sugarbeet, Celery, Soybean, Alfalfa, Medicago, Lotus, Vigna, Cucumber, Carrot, Eggplant, Cauliflower, Horseradish, Morning Glory, Poplar, Walnut, Apple, Asparagus, Rice, Corn, Millet, Onion, Barley, Orchard grass, Oat, Rye, and Wheat.

Such cells are available from a wide range of sources including: the American Type Culture Collection (Rockland, Md.); Chlamydomonas Culture Collection, (Duke University), Durham, N.C.; or from any of a number seed companies, e.g., W. Atlee Burpee Seed Co. (Warminster, Pa.), Park Seed Co. (Greenwood, S.C.), Johnny Seed Co. (Albion, Me.), or Northrup King Seeds (Harstville, S.C.). Descriptions and sources of useful host cells are also found in Vasil I.K., *Cell Culture and Somatic Cell Genetics of Plants*, Vol I, II, III Laboratory Procedures and Their Applications Academic Press, New York, 1984; Dixon, R. A., *Plant Cell Culture-A Practical Approach*, IRL Press, Oxford University, 1985; Green et al., *Plant Tissue and Cell Culture*, Academic Press, New York, 1987; Gasser and Fraley, Science 244: 1293, 1989.

For prokaryotic expression, DNA encoding an AFT1 polypeptide of the invention is carried on a vector operably linked to control signals capable of effecting expression in the prokaryotic host. If desired, the coding sequence may contain, at its 5' end, a sequence encoding any of the known signal sequences capable of effecting secretion of the expressed protein into the periplasmic space of the host cell, thereby facilitating recovery of the protein and subsequent purification. Prokaryotes most frequently used are various strains of *E. coli*; however, other microbial strains may also be used. Plasmid vectors are used which contain replication origins, selectable markers, and control sequences derived from a species compatible with the microbial host. Examples of such vectors may be found in Pouwels et al. (supra) or Ausubel et al. (supra). Commonly used prokaryotic control sequences (also referred to as "regulatory elements") are defined herein to include promoters for transcription initiation, optionally with an operator, along with ribosome binding site sequences. Promoters commonly used to direct protein expression include the beta-lactamase (penicillinase), the lactose (lac) (Chang et al., Nature 198: 1056, 1977), the tryptophan (Trp) (Goeddel et al., Nucl. Acids Res. 8: 4057, 1980) and the tac promoter systems as well as the lambda-derived $P_L$ promoter and N-gene ribosome binding site (Simatake et al., Nature 292: 128, 1981).

For eukaryotic expression, the method of transformation or transfection and the choice of vehicle for expression of the AFT1 polypeptide or chimeric activator protein will depend on the host system selected. Transformation and transfection methods are described, e.g., in Ausubel et al. (supra); Weissbach and Weissbach, *Methods for Plant Molecular Biology*, Academic Press, 1989; Gelvin et al., *Plant Molecular Biology Manual*, Kluwer Academic Publishers, 1990; Kindle, K., Proc. Natl. Acad. Sci., USA 87: 1228, 1990; Potrykus, I., *Annu. Rev. Plant Physiol. Plant Mol. Biology* 42: 205, 1991; and BioRad (Hercules, Calif.) Technical Bulletin #1687 (Biolistic Particle Delivery Systems). Expression vehicles may be chosen from those provided, e.g., in *Cloning Vectors*: A Laboratory Manual (P. H. Pouwels et al., 1985, Supp. 1987); Gasser and Fraley (supra); Clontech Molecular Biology Catalog (Catalog 1992/93 Tools for the Molecular Biologist, Palo Alto, Calif.); and the references cited above.

One preferred eukaryotic expression system is the mouse 3T3 fibroblast host cell transfected with a pMAMneo expression vector (Clontech, Palo Alto, Calif.). pMAMneo provides: an RSV-LTR enhancer linked to a dexamethasone-inducible MMTV-LTR promotor, an SV40 origin of replication which allows replication in mammalian systems, a selectable neomycin gene, and SV40 splicing and polyadenylation sites. DNA encoding an AFT1 polypeptide would be inserted into the pMAMneo vector in an orientation designed to allow expression. The recombinant AFT1 protein would be isolated as described below. Other preferable host cells which may be used in conjunction with the pMAMneo expression vehicle include COS cells and CHO cells (ATCC Accession Nos. CRL 1650 and CCL 61, respectively).

Alternatively, an AFT1 polypeptide is produced by a stably-transfected mammalian cell line. A number of vectors suitable for stable transfection of mammalian cells are available to the public, e.g., see Pouwels et al. (supra); methods for constructing such cell lines are also publicly available, e.g., in Ausubel et al. (supra). In one example, cDNA encoding the AFT1 polypeptide is cloned into an expression vector which includes the dihydrofolate reductase (DHFR) gene. Integration of the plasmid and, therefore, the AFT1-encoding gene into the host cell chromosome is selected for by inclusion of 0.01–300 μM methotrexate in the cell culture medium (as described in Ausubel et al., supra). This dominant selection can be accomplished in most cell types. Recombinant protein expression can be increased by DHFR-mediated amplification of the transfected gene. Methods for selecting cell lines bearing gene amplifications are described in Ausubel et al. (supra); such methods generally involve extended culture in medium containing gradually increasing levels of methotrexate. DHFR-containing expression vectors commonly used for this purpose include pCVSEII-DHRF and pAdD26SV(A) (described in Ausubel et al., supra). Any of the host cells described above or, preferably, a DHFR-deficient CHO cell line (e.g., CHO DHFR⁺ cells, ATCC Accession No. CRL 9096) are among the host cells preferred for DHFR selection of a stably-transfected cell line or DHFR-mediated gene amplification.

Most preferably, an AFT1 polypeptide or AFT1 chimeric transcriptional activator is produced by a stably-transfected plant cell line or by a transgenic plant. A number of vectors suitable for stable transfection of plant cells or for the establishment of transgenic plants are available to the public; such vectors are described in Pouwels et al. (supra), Weissbach and Weissbach (supra), and Gelvin et al. (supra). Methods for constructing such cell lines are described in, e.g., Weissbach and Weissbach (supra), and Gelvin et al. (Supra). Typically, plant expression vectors include (1) a cloned plant gene under the transcriptional control of 5' and 3' regulatory sequences and (2) a dominant selectable marker. Such plant expression vectors may also contain, if desired, a promoter regulatory region (e.g., one conferring inducible or constitutive, environmentally- or developmentally-regulated, or cell- or tissue-specific expression), a transcription initiation start site, a ribosome binding site, an RNA processing signal, a transcription termination site, and/or a polyadenylation signal.

Once the desired AFT1 nucleic acid sequences is obtained it may be manipulated in a variety of ways known in the art. For example, where the sequence involves non-coding flanking regions, the flanking regions maybe subjected to mutagenesis.

The AFT1 DNA sequence of the invention may, if desired, be combined with other DNA sequences in a variety of ways. The AFT1 DNA sequence of the invention may be employed with all or part of the gene sequences normally associated with the AFT1 protein. In its component parts a DNA sequence encoding an AFT1 protein is combined in the DNA construct having a transcription initiation control region capable of promoting transcription and translation in a host cell.

In general, the constructs will involve regulatory regions functional in plants which provide for modified production of AFT1 protein or a chimeric AFT1 protein as discussed Supra. The open reading frame coding for the AFT1 protein or functional fragment thereof will be joined at its 5' end to a transcription initiation regulatory region such as the sequence naturally found in the 5' upstream region of the AFT1 structural gene. Numerous other transcription initiation regions are available which provide for constitutive or inducible regulation.

For applications when developmental, hormonal or environmental expression is desired appropriate 5' upstream non-coding regions are obtained from other genes; for example, from genes regulated during seed development, embryo development, or leaf development.

Regulatory transcript termination regions may be also be provided in DNA constructs of this invention as well. Transcript termination regions may be provided by the DNA sequence encoding the AFT1 protein or any convenient transcription termination region derived from a different gene source, especially the transcript termination region which is normally associated with the transcript initiation region. The transcript termination region will contain preferably at least 1 kb, preferably about 3 kb of sequence 3' to the structurally gene from which the termination region is derived. Plant expression constructs having AFT1 as the DNA sequence of interest for expression thereof may be employed with a wide variety of plant life, particularly plant life involved in the production of seed storage proteins or storage lipids, useful for industrial and agricultural applications. Importantly, this invention is applicable to dicotyledons and monocotyledons, and will be readily applicable to any new or improved transformation or regeneration method.

An example of a useful plant promoter according to the invention is a caulimovirus promoter, e.g., a cauliflower mosaic virus (CaMV) promoter. These promoters confer high levels of expression in most plant tissues, and the activity of these promoters is not dependent on virally encoded proteins. CaMV is a source for both the 35S and 19S promoters. In most tissues of transgenic plants, the CaMV 35S promoter is a strong promoter (see, e.g., Odell et al., Nature 313: 810, 1985). The CaMV promoter is also highly active in monocots (see, e.g., Dekeyser et al., Plant Cell 2: 591, 1990; Terada and Shimamoto, Mol. Gen. Genet. 220: 389, 1990). Moreover, activity of this promoter can be further increased (i.e., between 2–10 fold) by duplication of the CaMV 35S promoter (see e.g., Kay et al., Science 236: 1299, 1987; Ow et al., Proc. Natl. Acad. Sci., USA 84: 4870, 1987; and Fang et al., Plant Cell 1: 141, 1989).

Other useful plant promoters include, without limitation, the nopaline synthase promoter (An et al., Plant Physiol. 88: 547, 1988) and the octopine synthase promoter (Fromm et al., Plant Cell 1: 977, 1989).

For certain applications, it may be desirable to produce the AFT1 gene product in an appropriate tissue, at an appropriate level, or at an appropriate developmental time. Thus, there are an assortment of gene promoters, each with its own distinct characteristics embodied in its regulatory sequences, shown to be regulated in response to the environment, hormones, and/or developmental cues. These include gene promoters that are responsible for (1) heat-regulated gene expression (see, e.g., Callis et al., Plant Physiol. 88: 965, 1988), (2) light-regulated gene expression (e.g., the pea rbcS-3A described by Kuhlemeier et al., Plant Cell 1: 471, 1989; the maize rbcS promoter described by Schaffner and Sheen, Plant Cell 3: 997, 1991; or the cholorphyll a/b-binding protein gene found in pea described by Simpson et al., EMBO J. 4: 2723, 1985), (3) hormone-regulated gene expression (e.g., the abscisic acid responsive sequences from the Em gene of wheat described by Marcotte et al., Plant Cell 1: 969, 1989), (4) wound-induced gene expression (e.g., of wunI described by Siebertz et al., Plant Cell 1: 961, 1989), or (5) organ-specific gene expression (e.g., of the tuber-specific storage protein gene described by Roshal et al., EMBO J. 6: 1155, 1987; the 23-kDa zein gene from maize described by Schernthaner et al., EMBO J. 7: 1249, 1988; or the French bean β-phaseolin gene described by Bustos et al., Plant Cell 1: 839, 1989).

Plant expression vectors may also optionally include RNA processing signals, e.g, introns, which have been shown to be important for efficient RNA synthesis and accumulation (Callis et al., Genes and Dev. 1: 1183, 1987). The location of the RNA splice sequences can dramatically influence the level of transgene expression in plants. In view of this fact, an intron may be positioned upstream or downstream of a AFT1 polypeptide-encoding sequence in the transgene to modulate levels of gene expression.

In addition to the aforementioned 5' regulatory control sequences, the expression vectors may also include regulatory control regions which are generally present in the 3' regions of plant genes (Thornburg et al., Proc. Natl. Acad. Sci. USA 84: 744, 1987; An et al., Plant Cell 1: 115, 1989). For example, the 3' terminator region may be included in the expression vector to increase stability of the mRNA. One such terminator region may be derived from the PI-II terminator region of potato. In addition, other commonly used terminators are derived from the octopine or nopaline synthase signals.

The plant expression vector also typically contains a dominant selectable marker gene used to identify those cells that have become transformed. Useful selectable genes for plant systems include genes encoding antibiotic resistance genes, for example, those encoding resistance to hygromycin, kanamycin, bleomycin, G418, streptomycin or spectinomycin. Genes required for photosynthesis may also be used as selectable markers in photosynthetic-deficient strains. Finally, genes encoding herbicide resistance may be used as selectable markers; useful herbicide resistance genes include the bar gene encoding the enzyme phosphinothricin acetyltransferase and conferring resistance to the broad spectrum herbicide Basta® (Hoechst AG, Frankfurt, Germany).

Efficient use of selectable markers is facilitated by a determination of the susceptibility of a plant cell to a particular selectable agent and a determination of the concentration of this agent which effectively kills most, if not all, of the transformed cells. Some useful concentrations of antibiotics for tobacco transformation include, e.g., 75–100 μg/ml (kanamycin), 20–50 μg/ml (hygromycin), or 5–10 μg/ml (bleomycin). A useful strategy for selection of transformants for herbicide resistance is described, e.g., by Vasil et al., supra.

It should be readily apparent to one skilled in the art of molecular biology, especially in the field of plant molecular biology, that the level of gene expression is dependent, not only on the combination of promoters, RNA processing signals and terminator elements, but also on how these elements are used to increase the levels of selectable marker gene expression.

Plant Transformation

Upon construction of the plant expression vector, several standard methods are accessible for introduction of the recombinant genetic material into the host plant for the generation of a transgenic plant. These methods include (1) Agrobacterium-mediated transformation (*A. tumefaciens* or *A. rhizogenes*) (see, e.g., Lichtenstein and Fuller In: *Genetic Engineering*, vol 6, PWJ Rigby, ed, London, Academic Press, 1987; and Lichtenstein, C. P., and Draper, J,. In: *DNA Cloning*, Vol II, D. M. Glover, ed, Oxford, IRI Press, 1985), (2) the particle delivery system (see, e.g., Gordon-Kamm et al., Plant Cell 2: 603, 1990; or BioRad Technical Bulletin 1687, supra), (3) microinjection protocols (see, e.g., Green et al., supra), (4) polyethylene glycol (PEG) procedures (see, e.g., Draper et al., Plant Cell Physiol. 23: 451, 1982; or e.g., Zhang and Wu, Theor. Appl. Genet. 76: 835, 1988), (5) liposome-mediated DNA uptake (see, e.g., Freeman et al., Plant Cell Physiol. 25: 1353, 1984), (6) electroporation protocols (see, e.g., Gelvin et al., supra; Dekeyser et al., supra; or Fromm et al., Nature 319: 791, 1986), and (7) the vortexing method (see, e.g., Kindle supra). The method of transformation is not critical to the instant invention; various method of plant transformation are currently available (supra). As newer methods are available to transform crops or other host cells they may be directly applied. Accordingly, a wide variety of methods have been developed to insert a DNA sequence into the gene of a plant host to obtain the transcription or transcript and translation of the sequence to effect phenotypic changes in both dicots and monocots. Moreover, the manner in which the DNA construct is introduced into the plant host is not critical to the invention. Thus, any method which provides for efficient transformation maybe employed.

The following is an example outlining an Agrobacterium-mediated plant transformation. The general process for manipulating genes to be transferred into the genome of plant cells is carried out in two phases. First, all the cloning and DNA modification steps are done in *E. coli*, and the plasmid containing the gene construct of interest is transferred by conjugation into Agrobacterium. Second, the resulting Agrobacterium strain is used to transform plant cells. Thus, for the generalized plant expression vector, the plasmid contains an origin of replication that allows it to replicate in Agrobacterium and a high copy number origin of replication functional in *E. coli*. This permits facile production and testing of transgenes in *E. coli* prior to transfer to Agrobacterium for subsequent introduction into plants. Resistance genes can be carried on the vector, one for selection in bacteria, e.g., streptomycin, and the other that will express in plants, e.g., a gene encoding for kanamycin resistance or an herbicide resistance gene. Also present are restriction endonuclease sites for the addition of one or more transgenes operably linked to appropriate regulatory sequences and directional T-DNA border sequences which, when recognized by the transfer functions of Agrobacterium, delimit the region that will be transferred to the plant.

In another example, plants cells may be transformed by shooting into the cell tungsten microprojectiles on which cloned DNA is precipitated. In the Biolistic Apparatus (Bio-Rad, Hercules, Calif.) used for the shooting, a gunpowder charge (22 caliber Power Piston Tool Charge) or an air-driven blast drives a plastic macroprojectile through a gun barrel. An aliquot of a suspension of tungsten particles on which DNA has been precipitated is placed on the front of the plastic macroprojectile. The latter is fired at an acrylic stopping plate that has a hole through it that is too small for the macroprojectile to go through. As a result, the plastic macroprojectile smashes against the stopping plate and the tungsten microprojectiles continue toward their target through the hole in the plate. For the instant invention the target can be any plant cell, tissue, seed, or embryo. The DNA introduced into the cell on the microprojectiles becomes integrated into either the nucleus or the chloroplast.

Transfer and expression of transgenes in plant cells is now routine practice to those skilled in the art. It has become a major tool to carry out gene expression studies and to attempt to obtain improved plant varieties of agricultural or commercial interest.

Transgenic Plant Regeneration

Plants cells transformed with a plant expression vector can be regenerated, e.g., from single cells, callus tissue or leaf discs according to standard plant tissue culture techniques. It is well known in the art that various cells, tissues, and organs from almost any plant can be successfully cultured to regenerate an entire plant; such techniques are described, e.g., in Vasil supra; Green et al., supra; Weissbach and Weissbach, supra; and Gelvin et al., supra.

In one particular example, a cloned AFT1 polypeptide under the control of the 35S CaMV promoter and the nopaline synthase terminator and carrying a selectable marker (e.g., kanamycin resistance) is transformed into Agrobacterium. Transformation of leaf discs (e.g., of tobacco leaf discs), with vector-containing Agrobacterium is carried out as described by Horsch et al. (Science 227: 1229, 1985). Putative transformants are selected after a few weeks (e.g., 3 to 5 weeks) on plant tissue culture media containing kanamycin (e.g. 100 µg/ml). Kanamycin-resistant shoots are then placed on plant tissue culture media without hormones for root initiation. Kanamycin-resistant plants are then selected for greenhouse growth. If desired, seeds from self-fertilized transgenic plants can then be sowed in a soil-less media and grown in a greenhouse. Kanamycin-resistant progeny are selected by sowing surfaced sterilized seeds on hormone-free kanamycin-containing media. Analysis for the integration of the transgene is accomplished by standard techniques (see, e.g., Ausubel et al. supra; Gelvin et al. supra).

Transgenic plants expressing the selectable marker are then screened for transmission of the transgene DNA by standard immunoblot and DNA detection techniques. Each positive transgenic plant and its transgenic progeny are unique in comparison to other transgenic plants established with the same transgene. Integration of the transgene DNA into the plant genomic DNA is in most cases random and the site of integration can profoundly effect the levels, and the tissue and developmental patterns of transgene expression. Consequently, a number of transgenic lines are usually screened for each transgene to identify and select plants with the most appropriate expression profiles.

Transgenic lines are evaluated on levels of transgene expression. Expression at the RNA level is determined initially to identify and quantitate expression-positive plants. Standard techniques for RNA analysis are employed and include PCR amplification assays using oligonucleotide primers designed to amplify only transgene RNA templates and solution hybridization assays using transgene-specific probes (see, e.g., Ausubel et al., supra). The RNA-positive plants are then analyzed for protein expression by Western immunoblot analysis using AFT1 specific antibodies (see, e.g., Ausubel et al., supra). In addition, in situ hybridization and immunocytochemistry according to standard protocols can be done using transgene-specific nucleotide probes and antibodies, respectively, to localize sites of expression within transgenic tissue.

Once the recombinant AFT1 protein is expressed in any cell or in a transgenic plant (e.g., as described above), it may be isolated, e.g., using affinity chromatography. In one example, an anti-AFT1 antibody (e.g., produced as described in Ausubel et al., supra, or by any standard technique) may be attached to a column and used to isolate the polypeptide. Lysis and fractionation of AFT1-producing cells prior to affinity chromatography may be performed by standard methods (see, e.g., Ausubel et al., supra). Once isolated, the recombinant protein can, if desired, be further purified, e.g., by high performance liquid chromatography (see, e.g., Fisher, *Laboratory Techniques In Biochemistry And Molecular Biology*, eds., Work and Burdon, Elsevier, 1980).

These general techniques of polypeptide expression and purification can also be used to produce and isolate useful AFT1 fragments or analogs.

In other applications, however, expression of the transgene in the plant cell or the transgenic plant may be the desired result. These include applications such as AFT1 controlled regulation of modulating plant defense related proteins, e.g., 3-O-methyltransferase or ascorbate peroxidase, or altering the normal development of the plant.

Use

Introduction of AFT1 or a chimeric AFT1 transcriptional activator into a transformed plant cell facilitates the manipulation of developmental events. For example, transgenic plants of the instant invention expressing AFT1 or an AFT1 chimeric transcriptional activator might be used to alter, simply and inexpensively, or regulate plant gene expression, e.g., plant defense mechanism, expression of plant storage components, or any number of other plant developmental events.

Other Embodiments

The invention also includes any biologically active fragment or analog of a crucifer AFT1 protein. By "biologically active" is meant possessing any in vivo or in vitro activity which is characteristic of the crucifer AFT1 polypeptide shown in FIG. 1 (SEQ ID NO: 2). Because crucifer AFT1 protein exhibits a range of physiological properties and because such properties may be attributable to different portions of the crucifer AFT1 protein molecule, a useful AFT1 fragment or analog is one which exhibits a biological activity in any biological assay for AFT1 transcriptional activation or binding activity, for example, those assays described supra. Such fragment or analog may function in accordance with developmental stages of different cell types and in response to different environmental factors and hormonal cues, or in response to a particular signal transduction pathway.

Preferred analogs include AFT1 proteins (or biologically active fragments thereof) whose sequences differ from the wild-type sequence only by conservative amino acid substitutions, for example, substitution of one amino acid for another with similar characteristics (e.g., valine for glycine, arginine for lysine, etc.) or by one or more non-conservative amino acid substitutions, deletions, or insertions which do not abolish the polypeptide's biological activity.

Analogs can differ from naturally occurring AFT1 protein in amino acid sequence or can be modified in ways that do not involve sequence, or both. Analogs of the invention will generally exhibit at least 70%, preferably 80%, more preferably 90%, and most preferably 95% or even 99%, homology with a segment of 20 amino acid residues, preferably 40 amino acid residues, or more preferably the entire sequence of a naturally occurring AFT1 polypeptide sequence.

Alterations in primary sequence include genetic variants, both natural and induced. Also included are analogs that include residues other than naturally occurring L-amino acids, e.g., D-amino acids or non-naturally occurring or synthetic amino acids, e.g., β or γ amino acids. Alternatively, increased stability may be conferred by cyclizing the peptide molecule. Also included in the invention are crucifer AFT1 proteins modified by in vivo or in vitro chemical derivatization of polypeptides, including acetylation, methylation, phosphorylation, carboxylation, or glycosylation.

In addition to substantially full-length polypeptides, the invention also includes biologically active fragments of the polypeptides. As used herein, the term "fragment", as applied to a polypeptide, will ordinarily be at least 20 residues, more typically at least 40 residues, and preferably at least 60 residues in length. Fragments of crucifer AFT1 proteins can be generated by methods known to those skilled in the art. The ability of a candidate fragment to exhibit a biological activity of crucifer AFT1 protein can be assessed by those methods described herein. Also included in the invention are crucifer AFT1 proteins containing residues that are not required for biological activity of the peptide, e.g., those added by alternative mRNA splicing or alternative protein processing events.

Other embodiments are within the following claims.

What is claimed is:

1. A substantially pure recombinant polypeptide comprising an amino acid sequence having at least 90% amino acid identity to the amino acid sequence of AFT1 polypeptide shown in FIG. 1 (SEQ ID NO: 2) and having the same biological activity as said AFT1 polypeptide.

2. A substantially pure recombinant polypeptide which is a fragment of an AFT1 polypeptide comprising a domain capable of activating transcription wherein said polypeptide is AFT1 (34-248) (SEQ ID NO: 27) or AFT1 (122-248) (SEQ ID NO: 28).

3. The substantially pure polypeptide of claim 1, wherein said polypeptide is derived from a crucifer.

4. The substantially pure polypeptide of claim 3, wherein said polypeptide is derived from Arabidopsis.

5. A substantially pure recombinant polypeptide which is a fragment of an AFT1 polypeptide comprising a domain capable of interacting with a plant defense related protein wherein said polypeptide is AFT1 (33-194)(SEQ ID NO: 29).

6. The substantially pure polypeptide of claim 1 wherein said polypeptide has the amino acid sequence shown in FIG. 1 (SEQ ID NO: 2).

* * * * *

UNITED STATES PATENT AND TRADEMARK OFFICE
CERTIFICATE OF CORRECTION

PATENT NO. : 5,623,054
DATED : April 22, 1997
INVENTORS : Hong Zhang et al.

It is certified that error appears in the above-identified patent and that said Letters Patent is hereby corrected as shown below:

Column 10, line 18, replace "m/RNA" with --mRNA--;

Column 15, line 42, replace "Supra" with --supra--.

Signed and Sealed this

Sixteenth Day of September, 1997

Attest:

BRUCE LEHMAN

*Attesting Officer*  *Commissioner of Patents and Trademarks*

SEQUENCE LISTING ( 1 ) GENERAL INFORMATION:

( i i i ) NUMBER OF SEQUENCES: 29

( 2 ) INFORMATION FOR SEQ ID NO: 1:

( i ) SEQUENCE CHARACTERISTICS:
        ( A ) LENGTH: 845
        ( B ) TYPE: nucleic acid
        ( C ) STRANDEDNESS: single
        ( D ) TOPOLOGY: linear ( x i ) SEQUENCE DESCRIPTION: SEQ ID NO: 1:

```
AAAAAAAAAT  CAAATCTCTC  TCTTTCTCTC  TCTAATGGCG  GCGACATTAG  GCAGAGACCA      60
GTATGTGTAC  ATGGCGAAGC  TCGCCGAGCA  GGCGGAGCGT  TACGAAGAGA  TGGTTCAATT     120
CATGGAACAG  CTCGTTACAG  GCGCTACTCC  AGCGGAAGAG  CTCACCGTTG  AAGAGAGGAA     180
TCTCCTCTCT  GTTGCTTACA  AGAACGTGAT  CGGATCTCTA  CGCGCCGCCT  GGAGGATCGT     240
GTCTTCGATT  GAGCAGAAGG  AAGAGAGTAG  GAAGAACGAC  GAGCACGTGT  CGCTTGTCAA     300
GGATTACAGA  TCTAAAGTTG  AGTCTGAGCT  TTCTTCTGTT  TGCTCTGGAA  TCCTTAAGCT     360
CCTTGACTCG  CATCTGATCC  CATCTGCTGG  AGCGAGTGAG  TCTAAGGTCT  TTTACTTGAA     420
GATGAAAGGT  GATTATCATC  GGTACATGGC  TGAGTTTAAG  TCTGGTGATG  AGAGGAAAAC     480
TGCTGCTGAA  GATACCATGC  TCGCTTACAA  AGCAGCTCAG  GATATCGCAG  CTGCGGATAT     540
GGCACCTACT  CATCCGATAA  GGCTTGGTCT  GGCCCTGAAT  TTCTCAGTGT  TCTACTATGA     600
GATTCTCAAT  TCTTCAGACA  AGCTTGTAA   CATGGCCAAA  CAGGCTTTTG  AGGAGGCCAT     660
AGCTGAGCTT  GACACTCTGG  GAGAGGAATC  CTACAAAGAC  AGCACTCTCA  TAATGCAGTT     720
GCTGAGGGAC  AATTTAACCC  TTTGGACCTC  CGATATGCAG  GAGCAGATGG  ACGAGGCCTG     780
AGGATCTAGA  TGAAGGGGGG  GAGGGTTGTT  ACGCGATGTT  TCTGCCACCA  AATCGATCTC     840
AAAAT                                                                      845
```

( 2 ) INFORMATION FOR SEQ ID NO: 2:

( i ) SEQUENCE CHARACTERISTICS:
        ( A ) LENGTH: 248
        ( B ) TYPE: amino acid
        ( C ) STRANDEDNESS: single
        ( D ) TOPOLOGY: linear ( x i ) SEQUENCE DESCRIPTION: SEQ ID NO: 2:

```
Met  Ala  Ala  Thr  Leu  Gly  Arg  Asp  Gln  Tyr  Val  Tyr  Met  Ala  Lys  Leu
 1              5                        10                       15

Ala  Glu  Gln  Ala  Glu  Arg  Tyr  Glu  Glu  Met  Val  Gln  Phe  Met  Glu  Gln
              20                        25                       30

Leu  Val  Thr  Gly  Ala  Thr  Pro  Ala  Glu  Glu  Leu  Thr  Val  Glu  Glu  Arg
          35                        40                       45

Asn  Leu  Leu  Ser  Val  Ala  Tyr  Lys  Asn  Val  Ile  Gly  Ser  Leu  Arg  Ala
      50                        55                       60

Ala  Trp  Arg  Ile  Val  Ser  Ser  Ile  Glu  Gln  Lys  Glu  Glu  Ser  Arg  Lys
65                        70                       75                       80

Asn  Asp  Glu  His  Val  Ser  Leu  Val  Lys  Asp  Tyr  Arg  Ser  Lys  Val  Glu
                  85                        90                       95

Ser  Glu  Leu  Ser  Ser  Val  Cys  Ser  Gly  Ile  Leu  Lys  Leu  Leu  Asp  Ser
             100                       105                      110
```

| His | Leu | Ile | Pro | Ser | Ala | Gly | Ala | Ser | Glu | Ser | Lys | Val | Phe | Tyr | Leu |
|---|---|---|---|---|---|---|---|---|---|---|---|---|---|---|---|
| | | 115 | | | | | 120 | | | | 125 | | | | |

| Lys | Met | Lys | Gly | Asp | Tyr | His | Arg | Tyr | Met | Ala | Glu | Phe | Lys | Ser | Gly |
|---|---|---|---|---|---|---|---|---|---|---|---|---|---|---|---|
| | 130 | | | | | 135 | | | | 140 | | | | | |

| Asp | Glu | Arg | Lys | Thr | Ala | Ala | Glu | Asp | Thr | Met | Leu | Ala | Tyr | Lys | Ala |
|---|---|---|---|---|---|---|---|---|---|---|---|---|---|---|---|
| 145 | | | | | 150 | | | | | 155 | | | | | 160 |

| Ala | Gln | Asp | Ile | Ala | Ala | Ala | Asp | Met | Ala | Pro | Thr | His | Pro | Ile | Arg |
|---|---|---|---|---|---|---|---|---|---|---|---|---|---|---|---|
| | | | | 165 | | | | 170 | | | | | | 175 | |

| Leu | Gly | Leu | Ala | Leu | Asn | Phe | Ser | Val | Phe | Tyr | Tyr | Glu | Ile | Leu | Asn |
|---|---|---|---|---|---|---|---|---|---|---|---|---|---|---|---|
| | | | 180 | | | | | 185 | | | | | 190 | | |

| Ser | Ser | Asp | Lys | Ala | Cys | Asn | Met | Ala | Lys | Gln | Ala | Phe | Glu | Glu | Ala |
|---|---|---|---|---|---|---|---|---|---|---|---|---|---|---|---|
| | | 195 | | | | | 200 | | | | | 205 | | | |

| Ile | Ala | Glu | Leu | Asp | Thr | Leu | Gly | Glu | Glu | Ser | Tyr | Lys | Asp | Ser | Thr |
|---|---|---|---|---|---|---|---|---|---|---|---|---|---|---|---|
| | 210 | | | | | 215 | | | | | 220 | | | | |

| Leu | Ile | Met | Gln | Leu | Leu | Arg | Asp | Asn | Leu | Thr | Leu | Trp | Thr | Ser | Asp |
|---|---|---|---|---|---|---|---|---|---|---|---|---|---|---|---|
| 225 | | | | | 230 | | | | | 235 | | | | | 240 |

| Met | Gln | Glu | Gln | Met | Asp | Glu | Ala |
|---|---|---|---|---|---|---|---|
| | | | | 245 | | | |

( 2 ) INFORMATION FOR SEQ ID NO: 3:

( i ) SEQUENCE CHARACTERISTICS:
        ( A ) LENGTH: 27
        ( B ) TYPE: nucleic acid
        ( C ) STRANDEDNESS: single
        ( D ) TOPOLOGY: linear ( x i ) SEQUENCE DESCRIPTION: SEQ ID NO: 3:

GCGGAATTCA TGAGGCCCAT TAAAATT          27

( 2 ) INFORMATION FOR SEQ ID NO: 4:

( i ) SEQUENCE CHARACTERISTICS:
        ( A ) LENGTH: 27
        ( B ) TYPE: nucleic acid
        ( C ) STRANDEDNESS: single
        ( D ) TOPOLOGY: linear ( x i ) SEQUENCE DESCRIPTION: SEQ ID NO: 4:

GTAGGATCCG GTCGGATTTC TTGTCGC          27

( 2 ) INFORMATION FOR SEQ ID NO: 5:

( i ) SEQUENCE CHARACTERISTICS:
        ( A ) LENGTH: 27
        ( B ) TYPE: nucleic acid
        ( C ) STRANDEDNESS: single
        ( D ) TOPOLOGY: linear ( x i ) SEQUENCE DESCRIPTION: SEQ ID NO: 5:

CGCGAATTCA ATAGCGACAA GTACGAT          27

( 2 ) INFORMATION FOR SEQ ID NO: 6:

( i ) SEQUENCE CHARACTERISTICS:
        ( A ) LENGTH: 28
        ( B ) TYPE: nucleic acid
        ( C ) STRANDEDNESS: single
        ( D ) TOPOLOGY: linear ( x i ) SEQUENCE DESCRIPTION: SEQ ID NO: 6:

GTAGGATCCG TCTCTCTTCC AAGGTAGA          28

( 2 ) INFORMATION FOR SEQ ID NO: 7:

( i ) SEQUENCE CHARACTERISTICS:
        ( A ) LENGTH: 31
        ( B ) TYPE: nucleic acid
        ( C ) STRANDEDNESS: single
        ( D ) TOPOLOGY: linear ( x i ) SEQUENCE DESCRIPTION: SEQ ID NO: 7:

GATCCTAGAA TTCAAGAAGA ATCGGCGTGG C                         31

( 2 ) INFORMATION FOR SEQ ID NO: 8:

( i ) SEQUENCE CHARACTERISTICS:
        ( A ) LENGTH: 29
        ( B ) TYPE: nucleic acid
        ( C ) STRANDEDNESS: single
        ( D ) TOPOLOGY: linear ( x i ) SEQUENCE DESCRIPTION: SEQ ID NO: 8:

CTGACTGAAT TCATGGCGGC GACATTAGG                           29

( 2 ) INFORMATION FOR SEQ ID NO: 9:

( i ) SEQUENCE CHARACTERISTICS:
        ( A ) LENGTH: 29
        ( B ) TYPE: nucleic acid
        ( C ) STRANDEDNESS: single
        ( D ) TOPOLOGY: linear ( x i ) SEQUENCE DESCRIPTION: SEQ ID NO: 9:

GACTGAGTCG ACCCTTCATC TAGATCCTC                           29

( 2 ) INFORMATION FOR SEQ ID NO: 10:

( i ) SEQUENCE CHARACTERISTICS:
        ( A ) LENGTH: 30
        ( B ) TYPE: nucleic acid
        ( C ) STRANDEDNESS: single
        ( D ) TOPOLOGY: linear ( x i ) SEQUENCE DESCRIPTION: SEQ ID NO: 10:

GACTGACTCG AGCCTTCATC TAGATCCTCA                          30

( 2 ) INFORMATION FOR SEQ ID NO: 11:

( i ) SEQUENCE CHARACTERISTICS:
        ( A ) LENGTH: 29
        ( B ) TYPE: nucleic acid
        ( C ) STRANDEDNESS: single
        ( D ) TOPOLOGY: linear ( x i ) SEQUENCE DESCRIPTION: SEQ ID NO: 11:

CTGACTGAAT TCGAGTCTAA GGTCTTTAC                           29

( 2 ) INFORMATION FOR SEQ ID NO: 12:

( i ) SEQUENCE CHARACTERISTICS:
        ( A ) LENGTH: 30
        ( B ) TYPE: nucleic acid
        ( C ) STRANDEDNESS: single
        ( D ) TOPOLOGY: linear ( x i ) SEQUENCE DESCRIPTION: SEQ ID NO: 12:

GACTGACTCG AGACTCGCTC CAGCAGATGG                          30

( 2 ) INFORMATION FOR SEQ ID NO: 13:

( i ) SEQUENCE CHARACTERISTICS:
    ( A ) LENGTH: 30
    ( B ) TYPE: nucleic acid
    ( C ) STRANDEDNESS: single
    ( D ) TOPOLOGY: linear ( x i ) SEQUENCE DESCRIPTION: SEQ ID NO: 13:

```
GACTGACTCG AGTGAAGAAT TGAGAATCTC                                    30
```

( 2 ) INFORMATION FOR SEQ ID NO: 14:

( i ) SEQUENCE CHARACTERISTICS:
        ( A ) LENGTH: 30
        ( B ) TYPE: nucleic acid
        ( C ) STRANDEDNESS: single
        ( D ) TOPOLOGY: linear ( x i ) SEQUENCE DESCRIPTION: SEQ ID NO: 14:

```
GACTGAGTCG ACACTCGCTC CAGCAGATGG                                    30
```

( 2 ) INFORMATION FOR SEQ ID NO: 15:

( i ) SEQUENCE CHARACTERISTICS:
        ( A ) LENGTH: 30
        ( B ) TYPE: nucleic acid
        ( C ) STRANDEDNESS: single
        ( ·D ) TOPOLOGY: linear ( x i ) SEQUENCE DESCRIPTION: SEQ ID NO: 15:

```
GACTGAGTCG ACTGAAGAAT TGAGAATCTC                                    30
```

( 2 ) INFORMATION FOR SEQ ID NO: 16:

( i ) SEQUENCE CHARACTERISTICS:
        ( A ) LENGTH: 31
        ( B ) TYPE: nucleic acid
        ( C ) STRANDEDNESS: single
        ( D ) TOPOLOGY: linear ( x i ) SEQUENCE DESCRIPTION: SEQ ID NO: 16:

```
CTGACTGAAT TCGTTACAGG CGCTACTCCA G                                  31
```

( 2 ) INFORMATION FOR SEQ ID NO: 17:

( i ) SEQUENCE CHARACTERISTICS:
        ( A ) LENGTH: 557
        ( B ) TYPE: nucleic acid
        ( C ) STRANDEDNESS: single
        ( D ) TOPOLOGY: linear ( x i ) SEQUENCE DESCRIPTION: SEQ ID NO: 17:

```
TCACCCAGAG AGGTCAGGCT TTGATGGACC ATGGACCCAA GAGCCGCTGA AGTTTGACAA    60
CTCCTACTTC GTGGAACTGC TGAAAGGAGA ATCAGAGGGC TTGTTGAAAC TTCCAACTGA   120
CAAGACCTTA TTGGAAGACC CGGAGTTCCG TCGTCTTGTT GAGCTTTATG CAAAGGATGA   180
AGATGCATTC TTCAGAGACT ACGCGGAATC GCACAAGAAA CTCTCTGAGC TTGGTTTCAA   240
CCCAAACTCC TCAGCAGGCA AAGCAGTTGC AGACAGCACG ATTCTGGCAC AGAGTGCGTT   300
CGGGGTTGCA GTTGCTGCTG CGGTTGTGGC ATTTGGTTAC TTTTACGAGA TTCGGAAGAG   360
GATGAAGTAA ACGAAATAGG AAGGAAAACA CGAAGCAACG ATGCTCTTAT TTGGGTATTA   420
AAGAAACTAT TAATCGTCTA TCGAATCTAT TTTGCTGCTA CAAGATTCTA AACTCTTTGA   480
ATCCACGATT CCACTGTTTA GTAGTAAAAA AGTTAAAAAG TCAATATTTT GGGTCCGTGA   540
TTCATTTTTG CGATAAA                                                  557
```

( 2 ) INFORMATION FOR SEQ ID NO: 18:

( i ) SEQUENCE CHARACTERISTICS:
    ( A ) LENGTH: 122
    ( B ) TYPE: amino acid
    ( C ) STRANDEDNESS: single
    ( D ) TOPOLOGY: linear ( x i ) SEQUENCE DESCRIPTION: SEQ ID NO: 18:

```
His Pro Glu Arg Ser Gly Phe Asp Gly Pro Trp Thr Gln Glu Pro Leu
 1               5                  10                  15
Lys Phe Asp Asn Ser Tyr Phe Val Glu Leu Leu Lys Gly Glu Ser Glu
                20                  25                  30
Gly Leu Leu Lys Leu Pro Thr Asp Lys Thr Leu Leu Glu Asp Pro Glu
            35                  40                  45
Phe Arg Arg Leu Val Glu Leu Tyr Ala Lys Asp Glu Asp Ala Phe Phe
        50                  55                  60
Arg Asp Tyr Ala Glu Ser His Lys Lys Leu Ser Glu Leu Gly Phe Asn
65                  70                  75                  80
Pro Asn Ser Ser Ala Gly Lys Ala Val Ala Asp Ser Thr Ile Leu Ala
                85                  90                  95
Gln Ser Ala Phe Gly Val Ala Val Ala Ala Ala Val Val Ala Phe Gly
                100                 105                 110
Tyr Phe Tyr Glu Ile Arg Lys Arg Met Lys
            115                 120
```

( 2 ) INFORMATION FOR SEQ ID NO: 19:

( i ) SEQUENCE CHARACTERISTICS:
    ( A ) LENGTH: 478
    ( B ) TYPE: nucleic acid
    ( C ) STRANDEDNESS: single
    ( D ) TOPOLOGY: linear ( x i ) SEQUENCE DESCRIPTION: SEQ ID NO: 19:

```
GAGTGACGAA  CATTGCGTGA  AATTCTTGAA  GAACTGCTAC  GAGTCACTTC  CAGAGGATGG      60
AAAAGTGATA  TTAGCAGAGT  GTATTCTTCC  AGAGACACCA  GACTCAAGCC  TCTCAACCAA     120
ACAAGTAGTC  CATGTCGATT  GCATTATGTT  GGCTCACAAT  CCCGGAGGCA  AGAACGAAC     180
CGAGAAAGAG  TTTGAGGCAT  AGCCAAAGC   ATCAGGCTTC  AAGGGCATCA  AGTTGTCTG     240
CGACGCTTTT  GGTGTTAACC  TTATTGAGTT  ACTCAAGAAG  CTCTAAAAAC  AAACAATGTT    300
CCTATGAAGA  TGATTTATAT  GTAAACATTA  TCTCATATCT  CCTTCCACGG  TTCCAAAACT    360
ATGCTGTTTA  ATAATGGTTT  TTACAAGAAT  TTGATTATGA  GTTTGTATTT  TTGTTTGTTT    420
GGAACAAAAT  TATGTGATTA  TAGGGAAAAA  TAAAATGAGC  TATTATTGAA  GAAAAAAA     478
```

( 2 ) INFORMATION FOR SEQ ID NO: 20:

( i ) SEQUENCE CHARACTERISTICS:
    ( A ) LENGTH: 94
    ( B ) TYPE: amino acid
    ( C ) STRANDEDNESS: single
    ( D ) TOPOLOGY: linear ( x i ) SEQUENCE DESCRIPTION: SEQ ID NO: 20:

```
Ser Asp Glu His Cys Val Lys Phe Leu Lys Asn Cys Tyr Glu Ser Leu
 1               5                  10                  15
Pro Glu Asp Gly Lys Val Ile Leu Ala Glu Cys Ile Leu Pro Glu Thr
                20                  25                  30
Pro Asp Ser Ser Leu Ser Thr Lys Gln Val Val His Val Asp Cys Ile
```

|  | 35 |  | 40 |  | 45 |  |
|---|---|---|---|---|---|---|
| Met | Leu Ala His Asn Pro | Gly | Gly Lys Glu Arg | Thr | Glu Lys Glu Phe |  |
|  | 50 |  | 55 |  | 60 |  |
| Glu | Ala Leu Ala Lys Ala | Ser | Gly Phe Lys Gly | Ile | Lys Val Val Cys |  |
| 65 |  | 70 |  | 75 |  | 80 |
| Asp | Ala Phe Gly Val Asn | Leu | Ile Glu Leu Leu | Lys | Lys Leu |  |
|  |  | 85 |  | 90 |  |  |

( 2 ) INFORMATION FOR SEQ ID NO: 21:

( i ) SEQUENCE CHARACTERISTICS:
    ( A ) LENGTH: 1357
    ( B ) TYPE: nucleic acid
    ( C ) STRANDEDNESS: single
    ( D ) TOPOLOGY: linear ( x i ) SEQUENCE DESCRIPTION: SEQ ID NO: 21:

| CCAGATTATC | CCTCCCCCGA | ATTCGGCACG | AGGAAAAATC | CTCTTCTTTC | AGATGAGAAA | 60 |
|---|---|---|---|---|---|---|
| CCCAAATCGA | CGGAGGAGAA | TAAGAGTTCT | AAGCCGGAAT | CAGCTTCTGG | GAGTTCAACT | 120 |
| TCATCAGCTA | TGCCTGGCTT | GAATTTCAAT | GCTTTTGATT | TCTCTAATAT | GGCTAGTATT | 180 |
| CTCAACGATC | CTAGCATCAG | AGAAATGGCT | GAGCAAATAG | CTAAAGATCC | TGCCTTTAAC | 240 |
| CAATTGGCTG | AGCAGCTTCA | GAGATCTATT | CCTAACGCTG | GCCAGGAAGG | TGGTTTCCCT | 300 |
| AACTTTGATC | CTCAACAGTA | TGTCAATACA | ATGCAACAGG | TTATGCATAA | CCCTGAGTTT | 360 |
| AAGACAATGG | CCGAGAAACT | TGGTACCGCC | TTAGTTCAGG | ATCCACAAAT | GTCTCCTTTT | 420 |
| TTGGATGCTT | TCTCGAATCC | TGAAACAGCA | GAACACTTTA | CTGAGCGTAT | GGCGCGGATG | 480 |
| AAAGAAGATC | CAGAGTTGAA | ACCTATACTA | GATGAGATTG | ATGCTGGTGG | TCCTTCTGCC | 540 |
| ATGATGAAGT | ACTGGAATGA | TCCAGAAGTG | CTGAAAAAGC | TGGGTGAAGC | AATGGGTATG | 600 |
| CCTGTTGCTG | GCTTACCAGA | CCAGACTGTT | TCAGCTGAAC | CTGAGGTAGC | AGAAGAAGGT | 660 |
| GAAGAAGAAG | AGTCTATTGT | TCACCAAACT | GCCAGTCTTG | GTGATGTTGA | GGGTTTGAAA | 720 |
| GCTGCCTTGG | CATCTGGTGG | TAACAAAGAT | GAAGAAGATT | CTGAAGGAAG | GACAGCATTG | 780 |
| CATTTTGCTT | GTGGATACGG | CGAGTTGAAA | TGTGCTCAAG | TTCTTATCGA | TGCTGGAGCA | 840 |
| AGTGTTAATG | CGGTTGACAA | AAACAAGAAC | ACACCTCTGC | ATTATGCTGC | TGGTTACGGG | 900 |
| AGGAAAGAGA | GTGTAAGCCT | TCTCCTGGAG | AATGGTGCTG | CAGTCACTCT | GCAAAACCTA | 960 |
| GACGAGAAGA | CGCCAATTGA | TGTAGCGAAG | CTCAACAGCC | AGCTGGAGGT | GGTGAAGCTG | 1020 |
| CTTGAGAAGG | ATGCTTTCCT | TTGAGCTCTG | CTGGTTAAAG | GAAAGCTCTA | AGCTCATATT | 1080 |
| GTCTTTGAGG | CATTTGTCTT | GTGTGTGTCC | TGAACCAGTT | TCACAGGCTT | TTTGTGTACA | 1140 |
| CTTTTTATTA | GTTCCTCTCT | TCTTCTAAAT | TTGTCTCTTA | TGTTGTTTTA | AAAGTCAATA | 1200 |
| AAGAAAGAAA | TAGCAATCAA | TGATTTAATT | TATGATTATA | TTCTTTATTT | CGTCGACCTC | 1260 |
| TACAGAATGA | TTCAATTTGG | AAGAATCATT | CTGGTTTGGA | GGATATGTAA | GAAAAACTAC | 1320 |
| TTGATCTCCA | AGTTATTCCA | TTCTTCTGTT | GAAAAAA |  |  | 1357 |

( 2 ) INFORMATION FOR SEQ ID NO: 22:

( i ) SEQUENCE CHARACTERISTICS:
    ( A ) LENGTH: 339
    ( B ) TYPE: amino acid
    ( C ) STRANDEDNESS: single
    ( D ) TOPOLOGY: linear ( x i ) SEQUENCE DESCRIPTION: SEQ ID NO: 22:

Gly Thr Arg Lys Asn Pro Leu Leu Ser Asp Glu Lys Pro Lys Ser Thr

|   | 1 |   |   |   | 5 |   |   |   |   | 10 |   |   |   |   | 15 |
|---|---|---|---|---|---|---|---|---|---|---|---|---|---|---|---|
| Glu | Glu | Asn | Lys | Ser | Ser | Lys | Pro | Glu | Ser | Ala | Ser | Gly | Ser | Ser | Thr |
|   |   |   | 20 |   |   |   |   | 25 |   |   |   | 30 |   |   |   |
| Ser | Ser | Ala | Met | Pro | Gly | Leu | Asn | Phe | Asn | Ala | Phe | Asp | Phe | Ser | Asn |
|   |   | 35 |   |   |   | 40 |   |   |   |   | 45 |   |   |   |   |
| Met | Ala | Ser | Ile | Leu | Asn | Asp | Pro | Ser | Ile | Arg | Glu | Met | Ala | Glu | Gln |
| 50 |   |   |   |   | 55 |   |   |   |   | 60 |   |   |   |   |   |
| Ile | Ala | Lys | Asp | Pro | Ala | Phe | Asn | Gln | Leu | Ala | Glu | Gln | Leu | Gln | Arg |
| 65 |   |   |   | 70 |   |   |   |   | 75 |   |   |   |   |   | 80 |
| Ser | Ile | Pro | Asn | Ala | Gly | Gln | Glu | Gly | Gly | Phe | Pro | Asn | Phe | Asp | Pro |
|   |   |   |   | 85 |   |   |   |   | 90 |   |   |   |   | 95 |   |
| Gln | Gln | Tyr | Val | Asn | Thr | Met | Gln | Gln | Val | Met | His | Asn | Pro | Glu | Phe |
|   |   |   | 100 |   |   |   |   | 105 |   |   |   |   | 110 |   |   |
| Lys | Thr | Met | Ala | Glu | Lys | Leu | Gly | Thr | Ala | Leu | Val | Gln | Asp | Pro | Gln |
|   |   | 115 |   |   |   |   | 120 |   |   |   |   | 125 |   |   |   |
| Met | Ser | Pro | Phe | Leu | Asp | Ala | Phe | Ser | Asn | Pro | Glu | Thr | Ala | Glu | His |
|   | 130 |   |   |   |   | 135 |   |   |   |   | 140 |   |   |   |   |
| Phe | Thr | Glu | Arg | Met | Ala | Arg | Met | Lys | Glu | Asp | Pro | Glu | Leu | Lys | Pro |
| 145 |   |   |   |   | 150 |   |   |   |   | 155 |   |   |   |   | 160 |
| Ile | Leu | Asp | Glu | Ile | Asp | Ala | Gly | Gly | Pro | Ser | Ala | Met | Met | Lys | Tyr |
|   |   |   |   | 165 |   |   |   |   | 170 |   |   |   |   | 175 |   |
| Trp | Asn | Asp | Pro | Glu | Val | Leu | Lys | Lys | Leu | Gly | Glu | Ala | Met | Gly | Met |
|   |   |   | 180 |   |   |   |   | 185 |   |   |   |   | 190 |   |   |
| Pro | Val | Ala | Gly | Leu | Pro | Asp | Gln | Thr | Val | Ser | Ala | Glu | Pro | Glu | Val |
|   |   | 195 |   |   |   |   | 200 |   |   |   |   | 205 |   |   |   |
| Ala | Glu | Glu | Gly | Glu | Glu | Glu | Glu | Ser | Ile | Val | His | Gln | Thr | Ala | Ser |
|   | 210 |   |   |   |   | 215 |   |   |   |   | 220 |   |   |   |   |
| Leu | Gly | Asp | Val | Glu | Gly | Leu | Lys | Ala | Ala | Leu | Ala | Ser | Gly | Gly | Asn |
| 225 |   |   |   |   | 230 |   |   |   |   | 235 |   |   |   |   | 240 |
| Lys | Asp | Glu | Glu | Asp | Ser | Glu | Gly | Arg | Thr | Ala | Leu | His | Phe | Ala | Cys |
|   |   |   |   | 245 |   |   |   |   | 250 |   |   |   |   | 255 |   |
| Gly | Tyr | Gly | Glu | Leu | Lys | Cys | Ala | Gln | Val | Leu | Ile | Asp | Ala | Gly | Ala |
|   |   |   | 260 |   |   |   |   | 265 |   |   |   |   | 270 |   |   |
| Ser | Val | Asn | Ala | Val | Asp | Lys | Asn | Lys | Asn | Thr | Pro | Leu | His | Tyr | Ala |
|   |   | 275 |   |   |   |   | 280 |   |   |   |   | 285 |   |   |   |
| Ala | Gly | Tyr | Gly | Arg | Lys | Glu | Ser | Val | Ser | Leu | Leu | Leu | Glu | Asn | Gly |
|   | 290 |   |   |   |   | 295 |   |   |   |   | 300 |   |   |   |   |
| Ala | Ala | Val | Thr | Leu | Gln | Asn | Leu | Asp | Glu | Lys | Thr | Pro | Ile | Asp | Val |
| 305 |   |   |   |   | 310 |   |   |   |   | 315 |   |   |   |   | 320 |
| Ala | Lys | Leu | Asn | Ser | Gln | Leu | Glu | Val | Val | Lys | Leu | Leu | Glu | Lys | Asp |
|   |   |   |   | 325 |   |   |   |   | 330 |   |   |   |   | 335 |   |
| Ala | Phe | Leu |   |   |   |   |   |   |   |   |   |   |   |   |   |

( 2 ) INFORMATION FOR SEQ ID NO: 23:

( i ) SEQUENCE CHARACTERISTICS:
        ( A ) LENGTH: 663
        ( B ) TYPE: nucleic acid
        ( C ) STRANDEDNESS: single
        ( D ) TOPOLOGY: linear ( x i ) SEQUENCE DESCRIPTION: SEQ ID NO: 23:

```
TTTTAAAAAA TTTTGCCATC AACCGTAGAT GTTCCGCCAA AGGGTGGGTT TAGCTTCGAT      60
CTGTGTAAGA GAAATGATAT TCTTACACAA AAGGGTCTTA AAGCTCCGTC TTTTTTGAAG     120
ACTGGAACAA CCATTGTTGG TTTGATTTTC AAGGATGGTG TGATACAAGG GGCAGATACC     180
```

| | | | | |
|---|---|---|---|---|
| CGAGCAACTG | AGGGGCCAAT | TGTTGCTGAT | AAGAACTGTG | AGAAGATTCA | CTATATGGCA | 240 |
| CCAAACATAT | ATTGCTGTGG | TGCAGGAACT | CGGGCTGATA | CTGAAGCAGT | CACTGATATG | 300 |
| GTCAGCTCAC | AGCTGCGATT | GCATCGTTAC | CAGACTGGTC | GAGACTCTCG | GGTCATTACT | 360 |
| GCTTTGACCC | TTCTCAAAAA | ACATTTTTTC | AGCTACCAAG | GTCATGTCTC | TGCTGCTCTT | 420 |
| GTACTCGGTG | GAGTTGATAT | CACTGGTCCA | CATCTGCATA | CTATATACCC | ACACGGTTCA | 480 |
| ACTGACACTC | TTCCATTCGC | CACAATGGGT | TCGGGTTCTC | TTGCTGCTAT | GTCTGTGTTT | 540 |
| GAGGCAAAGT | ATAAGAAGG | CCTAACTAGG | GATGAAGGAA | TTAAGCTGGT | CGCTGAATCC | 600 |
| ATATGCTCGG | GTATATCCAA | TGACCTGGGT | AGTGGTAGCA | ACGTGGACAT | CTGCGTGATC | 660 |
| ACA | | | | | | 663 |

( 2 ) INFORMATION FOR SEQ ID NO: 24:

( i ) SEQUENCE CHARACTERISTICS:
( A ) LENGTH: 219
( B ) TYPE: amino acid
( C ) STRANDEDNESS: single
( D ) TOPOLOGY: linear ( x i ) SEQUENCE DESCRIPTION: SEQ ID NO: 24:

```
Lys Ile Leu Pro Ser Thr Val Asp Val Pro Pro Lys Gly Gly Phe Ser
 1               5                  10                  15

Phe Asp Leu Cys Lys Arg Asn Asp Ile Leu Thr Gln Lys Gly Leu Lys
            20                  25                  30

Ala Pro Ser Phe Leu Lys Thr Gly Thr Thr Ile Val Gly Leu Ile Phe
        35                  40                  45

Lys Asp Gly Val Ile Gln Gly Ala Asp Thr Arg Ala Thr Glu Gly Pro
    50                  55                  60

Ile Val Ala Asp Lys Asn Cys Glu Lys Ile His Tyr Met Ala Pro Asn
65                  70                  75                  80

Ile Tyr Cys Cys Gly Ala Gly Thr Arg Ala Asp Thr Glu Ala Val Thr
                85                  90                  95

Asp Met Val Ser Ser Gln Leu Arg Leu His Arg Tyr Gln Thr Gly Arg
            100                 105                 110

Asp Ser Arg Val Ile Thr Ala Leu Thr Leu Leu Lys Lys His Phe Phe
        115                 120                 125

Ser Tyr Gln Gly His Val Ser Ala Ala Leu Val Leu Gly Gly Val Asp
    130                 135                 140

Ile Thr Gly Pro His Leu His Thr Ile Tyr Pro His Gly Ser Thr Asp
145                 150                 155                 160

Thr Leu Pro Phe Ala Thr Met Gly Ser Gly Ser Leu Ala Ala Met Ser
                165                 170                 175

Val Phe Glu Ala Lys Tyr Lys Glu Gly Leu Thr Arg Asp Glu Gly Ile
            180                 185                 190

Lys Leu Val Ala Glu Ser Ile Cys Ser Gly Ile Ser Asn Asp Leu Gly
        195                 200                 205

Ser Gly Ser Asn Val Asp Ile Cys Val Ile Thr
    210                 215
```

( 2 ) INFORMATION FOR SEQ ID NO: 25:

( i ) SEQUENCE CHARACTERISTICS:
( A ) LENGTH: 976
( B ) TYPE: nucleic acid
( C ) STRANDEDNESS: single
( D ) TOPOLOGY: linear ( x i ) SEQUENCE DESCRIPTION: SEQ ID NO: 25:

```
ACGAGAGGCC CTGAGACGCG GCAGATATCA GGTCCTGCGA CTTCAACACA GATCAGGAAC      60
TTCACATTAT GTCAGCATCT GCAAGGAATC CACACACATA TCTCATCCAT GGTAGCGGAC     120
CTTCCCAGTA TTGCTACTGA TGTATTGTCT CCTTATCTGG CTGCAATCTA TAATGCGGCA     180
TGTGAGCCAG TTACACCTTT GTTTAAAGCA ATGCGAGACA AGCTCGAGTC ATGCATTCTT     240
CAAATCCATG ATCAAAACTT TGGTGCTGAT GACGCTGACA TGGACAACAA CGCTTCCTCA     300
TACATGGAGG AGTTGCAGAG ATCGATTCTT CACTTCCGCA AGGAGTTCCT ATCTAGACTA     360
TTGCCTTCCG CAGCAAATGC TAACACTGCA GGAACAGAAT CGATCTGCAC AAGACTCACA     420
AGACAAATGG CGTCAAGGGT TTTGATCTTC TACATCAGAC ATGCATCCCT TGTGCGACCA     480
CTTTCAGAAT GGGGAAAACT CAGAATGGCC AAAGACATGG CCGAGCTGGA ACTAGCAGTG     540
GGACAGAATC TATTTCCCGT GGAACAACTC GGAGCACCGT ACAGAGCTCT TAGAGCGTTT     600
AGGCCTTTGG TTTTCCTGGA AACATCTCAA ATGGGATCAT CTCCTCTCAT CAATGATCTA     660
CCACCGAGCA TCGTCCTACA TCATCTCTAC ACAAGAGGCC CAGACGAGTT AGAGTCACCG     720
ATGCAGAAGA ACAGACTAAG TCCTAAACAG TACTCACTGT GGCTTGATAA CCAAAGAGAG     780
GATCAGATCT GGAAAGGGAT AAAAGCAACT TTGGATGATT ATGCAGTGAA GATCAGATCG     840
AGAGGGGACA AAGAGTTTAG TCCAGGTTAT CCTCTAATGC TTCAAATTGG TTCATCTTTA     900
ACACAAGAAA ACTTATAAGC TGTGCTTTGT TACCGAATCA ATATTCTTCT ATTGCGAACT     960
TTTTTGTCTC AAAAAA                                                     976
```

( 2 ) INFORMATION FOR SEQ ID NO: 26:

( i ) SEQUENCE CHARACTERISTICS:
        ( A ) LENGTH: 305
        ( B ) TYPE: amino acid
        ( C ) STRANDEDNESS: single
        ( D ) TOPOLOGY: linear ( x i ) SEQUENCE DESCRIPTION: SEQ ID NO: 26:

```
Thr Arg Gly Pro Glu Thr Arg Gln Ile Ser Gly Pro Ala Thr Ser Thr
 1               5                  10                  15

Gln Ile Arg Asn Phe Thr Leu Cys Gln His Leu Gln Gly Ile His Thr
                20                  25                  30

His Ile Ser Ser Met Val Ala Asp Leu Pro Ser Ile Ala Thr Asp Val
            35                  40                  45

Leu Ser Pro Tyr Leu Ala Ala Ile Tyr Asn Ala Ala Cys Glu Pro Val
        50                  55                  60

Thr Pro Leu Phe Lys Ala Met Arg Asp Lys Leu Glu Ser Cys Ile Leu
65                  70                  75                  80

Gln Ile His Asp Gln Asn Phe Gly Ala Asp Asp Ala Asp Met Asp Asn
                85                  90                  95

Asn Ala Ser Ser Tyr Met Glu Glu Leu Gln Arg Ser Ile Leu His Phe
            100                 105                 110

Arg Lys Glu Phe Leu Ser Arg Leu Leu Pro Ser Ala Ala Asn Ala Asn
        115                 120                 125

Thr Ala Gly Thr Glu Ser Ile Cys Thr Arg Leu Thr Arg Gln Met Ala
    130                 135                 140

Ser Arg Val Leu Ile Phe Tyr Ile Arg His Ala Ser Leu Val Arg Pro
145                 150                 155                 160

Leu Ser Glu Trp Gly Lys Leu Arg Met Ala Lys Asp Met Ala Glu Leu
                165                 170                 175
```

```
Glu  Leu  Ala  Val  Gly  Gln  Asn  Leu  Phe  Pro  Val  Glu  Gln  Leu  Gly  Ala
               180                      185                      190

Pro  Tyr  Arg  Ala  Leu  Arg  Ala  Phe  Arg  Pro  Leu  Val  Phe  Leu  Glu  Thr
               195                      200                      205

Ser  Gln  Met  Gly  Ser  Ser  Pro  Leu  Ile  Asn  Asp  Leu  Pro  Pro  Ser  Ile
     210                      215                      220

Val  Leu  His  His  Leu  Tyr  Thr  Arg  Gly  Pro  Asp  Glu  Leu  Glu  Ser  Pro
225                           230                      235                      240

Met  Gln  Lys  Asn  Arg  Leu  Ser  Pro  Lys  Gln  Tyr  Ser  Leu  Trp  Leu  Asp
                    245                      250                      255

Asn  Gln  Arg  Glu  Asp  Gln  Ile  Trp  Lys  Gly  Ile  Lys  Ala  Thr  Leu  Asp
               260                      265                      270

Asp  Tyr  Ala  Val  Lys  Ile  Arg  Ser  Arg  Gly  Asp  Lys  Glu  Phe  Ser  Pro
               275                      280                      285

Gly  Tyr  Pro  Leu  Met  Leu  Gln  Ile  Gly  Ser  Ser  Leu  Thr  Gln  Glu  Asn
               290                      295                      300

Leu.
305
```

( 2 ) INFORMATION FOR SEQ ID NO: 27:

( i ) SEQUENCE CHARACTERISTICS:
        ( A ) LENGTH: 215
        ( B ) TYPE: amino acid
        ( C ) STRANDEDNESS: single
        ( D ) TOPOLOGY: linear ( x i ) SEQUENCE DESCRIPTION: SEQ ID NO: 27:

```
Val  Thr  Gly  Ala  Thr  Pro  Ala  Glu  Glu  Leu  Thr  Val  Glu  Glu  Arg  Asn
1                        5                        10                       15

Leu  Leu  Ser  Val  Ala  Tyr  Lys  Asn  Val  Ile  Gly  Ser  Leu  Arg  Ala  Ala
               20                       25                       30

Trp  Arg  Ile  Val  Ser  Ser  Ile  Glu  Gln  Lys  Glu  Glu  Ser  Arg  Lys  Asn
               35                       40                       45

Asp  Glu  His  Val  Ser  Leu  Val  Lys  Asp  Tyr  Arg  Ser  Lys  Val  Glu  Ser
     50                       55                       60

Glu  Leu  Ser  Ser  Val  Cys  Ser  Gly  Ile  Leu  Lys  Leu  Leu  Asp  Ser  His
65                       70                       75                       80

Leu  Ile  Pro  Ser  Ala  Gly  Ala  Ser  Glu  Ser  Lys  Val  Phe  Tyr  Leu  Lys
                    85                       90                       95

Met  Lys  Gly  Asp  Tyr  His  Arg  Tyr  Met  Ala  Glu  Phe  Lys  Ser  Gly  Asp
               100                      105                      110

Glu  Arg  Lys  Thr  Ala  Ala  Glu  Asp  Thr  Met  Leu  Ala  Tyr  Lys  Ala  Ala
               115                      120                      125

Gln  Asp  Ile  Ala  Ala  Ala  Asp  Met  Ala  Pro  Thr  His  Pro  Ile  Arg  Leu
     130                      135                      140

Gly  Leu  Ala  Leu  Asn  Phe  Ser  Val  Phe  Tyr  Tyr  Glu  Ile  Leu  Asn  Ser
145                      150                      155                      160

Ser  Asp  Lys  Ala  Cys  Asn  Met  Ala  Lys  Gln  Ala  Phe  Glu  Glu  Ala  Ile
               165                      170                      175

Ala  Glu  Leu  Asp  Thr  Leu  Gly  Glu  Glu  Ser  Tyr  Lys  Asp  Ser  Thr  Leu
               180                      185                      190

Ile  Met  Gln  Leu  Leu  Arg  Asp  Asn  Leu  Thr  Leu  Trp  Thr  Ser  Asp  Met
               195                      200                      205

Gln  Glu  Gln  Met  Asp  Glu  Ala
```

( 2 ) INFORMATION FOR SEQ ID NO: 28:

( i ) SEQUENCE CHARACTERISTICS:
        ( A ) LENGTH: 127
        ( B ) TYPE: amino acid
        ( C ) STRANDEDNESS: single
        ( D ) TOPOLOGY: linear ( x i ) SEQUENCE DESCRIPTION: SEQ ID NO: 28:

```
Glu Ser Lys Val Phe Tyr Leu Lys Met Lys Gly Asp Tyr His Arg Tyr
 1               5                  10                  15
Met Ala Glu Phe Lys Ser Gly Asp Glu Arg Lys Thr Ala Ala Glu Asp
             20                  25                  30
Thr Met Leu Ala Tyr Lys Ala Ala Gln Asp Ile Ala Ala Ala Asp Met
         35                  40                  45
Ala Pro Thr His Pro Ile Arg Leu Gly Leu Ala Leu Asn Phe Ser Val
     50                  55                  60
Phe Tyr Tyr Glu Ile Leu Asn Ser Ser Asp Lys Ala Cys Asn Met Ala
 65                  70                  75                  80
Lys Gln Ala Phe Glu Glu Ala Ile Ala Glu Leu Asp Thr Leu Gly Glu
                 85                  90                  95
Glu Ser Tyr Lys Asp Ser Thr Leu Ile Met Gln Leu Leu Arg Asp Asn
             100                 105                 110
Leu Thr Leu Trp Thr Ser Asp Met Gln Glu Gln Met Asp Glu Ala
         115                 120                 125
```

( 2 ) INFORMATION FOR SEQ ID NO: 29:

( i ) SEQUENCE CHARACTERISTICS:
        ( A ) LENGTH: 162
        ( B ) TYPE: amino acid
        ( C ) STRANDEDNESS: single
        ( D ) TOPOLOGY: linear ( x i ) SEQUENCE DESCRIPTION: SEQ ID NO: 29:

```
Leu Val Thr Gly Ala Thr Pro Ala Glu Glu Leu Thr Val Glu Glu Arg
 1               5                  10                  15
Asn Leu Leu Ser Val Ala Tyr Lys Asn Val Ile Gly Ser Leu Arg Ala
             20                  25                  30
Ala Trp Arg Ile Val Ser Ser Ile Glu Gln Lys Glu Glu Ser Arg Lys
         35                  40                  45
Asn Asp Glu His Val Ser Leu Val Lys Asp Tyr Arg Ser Lys Val Glu
     50                  55                  60
Ser Glu Leu Ser Ser Val Cys Ser Gly Ile Leu Lys Leu Leu Asp Ser
 65                  70                  75                  80
His Leu Ile Pro Ser Ala Gly Ala Ser Glu Ser Lys Val Phe Tyr Leu
                 85                  90                  95
Lys Met Lys Gly Asp Tyr His Arg Tyr Met Ala Glu Phe Lys Ser Gly
             100                 105                 110
Asp Glu Arg Lys Thr Ala Ala Glu Asp Thr Met Leu Ala Tyr Lys Ala
             115                 120                 125
Ala Gln Asp Ile Ala Ala Ala Asp Met Ala Pro Thr His Pro Ile Arg
         130                 135                 140
Leu Gly Leu Ala Leu Asn Phe Ser Val Phe Tyr Tyr Glu Ile Leu Asn
145                 150                 155                 160
Ser Ser
```